United States Patent
Kiyan et al.

(10) Patent No.: US 10,568,604 B2
(45) Date of Patent: Feb. 25, 2020

(54) METHOD AND DEVICE FOR ULTRASONIC DIAGNOSIS

(71) Applicant: Furuno Electric Co., Ltd., Nishinomiya (JP)

(72) Inventors: Wataru Kiyan, Nishinomiya (JP); Satoshi Kawanami, Nishinomiya (JP)

(73) Assignee: Furuno Electric Co., Ltd., Nishinomiya (JP)

( * ) Notice: Subject to any disclaimer, the term of this patent is extended or adjusted under 35 U.S.C. 154(b) by 456 days.

(21) Appl. No.: 15/124,907

(22) PCT Filed: Feb. 26, 2015

(86) PCT No.: PCT/JP2015/055567
§ 371 (c)(1),
(2) Date: Sep. 9, 2016

(87) PCT Pub. No.: WO2015/137131
PCT Pub. Date: Sep. 17, 2015

(65) Prior Publication Data
US 2017/0035386 A1 Feb. 9, 2017

(30) Foreign Application Priority Data
Mar. 12, 2014 (JP) .................................. 2014-048884

(51) Int. Cl.
*A61B 8/00* (2006.01)
*A61B 8/08* (2006.01)
(Continued)

(52) U.S. Cl.
CPC .......... *A61B 8/0875* (2013.01); *A61B 8/5223* (2013.01); *G01S 7/52036* (2013.01);
(Continued)

(58) Field of Classification Search
CPC .................................................. A61B 5/4514
See application file for complete search history.

(56) References Cited

U.S. PATENT DOCUMENTS 4,932,415 A * 6/1990 Angelsen ................. A61B 8/06
600/455
5,458,130 A * 10/1995 Kaufman ............. A61B 8/0875
128/925

(Continued)

FOREIGN PATENT DOCUMENTS

CN 102525549 A 7/2012
EP 2454997 A1 5/2012
(Continued)

OTHER PUBLICATIONS

Mohamed, A. A. et al. (2010). The basics of echocardiography. Journal of Saudi Heart Association, 22, 71-76. , specifically p. 72, col. 2, section 6.*
(Continued)

*Primary Examiner* — Bill Thomson
*Assistant Examiner* — Aminah Asghar
(74) *Attorney, Agent, or Firm* — Alleman Hall Creasman & Tuttle LLP

(57) ABSTRACT

To accurately detect a shape and derive information of cartilage based on detected echoes, an ultrasonic diagnosing device includes an ultrasonic transmitter, an ultrasonic receiver, a low-frequency component extracting module, and a deriving module. The ultrasonic transmitter transmits ultrasonic waves to a cartilage in a plurality of bent states, in a state where a relative position of a wave transmitting and receiving surface to the cartilage is fixed. The ultrasonic receiver receives echo signals corresponding to respective frames in each of the plurality of bent states. The low-frequency component extracting module extracts, in a frame direction, low-frequency echo data which is echo data of a
(Continued)

frequency component below a given frequency. The deriving module derives information of the cartilage based on the low-frequency echo data.

14 Claims, 18 Drawing Sheets

(51) Int. Cl.
    *G01S 7/52*     (2006.01)
    *G01S 15/89*     (2006.01)

(52) U.S. Cl.
    CPC ...... *G01S 7/52071* (2013.01); *G01S 15/8915* (2013.01); *A61B 8/40* (2013.01); *A61B 8/461* (2013.01); *A61B 8/483* (2013.01)

(56) References Cited

U.S. PATENT DOCUMENTS

| | | | |
|---|---|---|---|
| 6,585,666 B2 | 7/2003 | Suh et al. | |
| 2004/0243003 A1* | 12/2004 | Pasternak | A61B 5/107 600/449 |
| 2010/0256504 A1* | 10/2010 | Moreau-Gaudry | A61B 5/0066 600/476 |
| 2011/0054313 A1* | 3/2011 | Kiyan | A61B 8/0875 600/437 |
| 2011/0208058 A1* | 8/2011 | Hughes | A61B 8/08 600/443 |
| 2012/0041446 A1* | 2/2012 | Wong | A61B 17/1703 606/96 |
| 2013/0211259 A1* | 8/2013 | Komistek | A61B 8/5223 600/440 |
| 2013/0217998 A1* | 8/2013 | Mahfouz | G16H 50/50 600/409 |
| 2014/0064591 A1* | 3/2014 | Sasaki | A61B 8/00 382/131 |
| 2015/0042677 A1* | 2/2015 | Shimamura | A61B 6/4233 345/632 |
| 2015/0190117 A1 | 7/2015 | Arai et al. | |

FOREIGN PATENT DOCUMENTS

| | | |
|---|---|---|
| JP | 2002345821 A | 12/2002 |
| JP | 2010000125 A | 1/2010 |
| JP | 2010017369 A | 1/2010 |
| JP | 2011125757 A | 6/2011 |
| WO | 2008108054 A1 | 9/2008 |
| WO | 2014013816 A1 | 1/2014 |
| WO | 2014045924 A1 | 3/2014 |

OTHER PUBLICATIONS

ISA Japan Patent Office, International Search Report Issued in Application No. PCT/JP2015/055567, dated May 19, 2015, WIPO, 4 pages.

* cited by examiner

METHOD AND DEVICE FOR ULTRASONIC DIAGNOSIS

TECHNICAL FIELD

This disclosure relates to a method and device for ultrasonic diagnosis, which diagnose a state of a cartilage.

BACKGROUND ART

Conventionally, ultrasonic diagnosing devices are known, which derive information of a cartilage based on reflection echoes caused by ultrasonic waves transmitted toward the cartilage, so as to analyze a state of the cartilage. For example, Patent Document 1 discloses an ultrasonic diagnosing device which extracts a boundary between a knee cartilage and a different tissue adjacent to the cartilage by extracting an edge of an echo level from echo signals of ultrasonic beams transmitted to the cartilage. Further, a shape of the cartilage is extracted based on the extracted boundary.

REFERENCE DOCUMENT OF CONVENTIONAL ART

Patent Document

Patent Document 1: JP2010-000125A

DESCRIPTION OF THE DISCLOSURE

Problems to be Solved by the Disclosure

However, when the cartilage and the different tissue adjacent thereto have a small difference in echo level, the above-described edge extraction may not be accurately performed and the estimation accuracy of the boundary between the two tissues may become low. In such a case, the shape of the cartilage cannot accurately be detected.

This disclosure is made in view of solving the subject described above and aims to accurately detect a shape of a cartilage and derive information of the cartilage based on echoes from the cartilage detected with high accuracy.

SUMMARY OF THE DISCLOSURE (1) In order to solve the subject described above, an ultrasonic diagnosing device according to one aspect of this disclosure includes an ultrasonic transmitter configured to transmit ultrasonic waves to a cartilage on an end part of a first bone through a soft tissue covering a joint including the end part of the first bone and an end part of a second bone, the ultrasonic transmitter transmitting the ultrasonic waves to the cartilage in a plurality of bent states with different bent angles of the second bone with respect to the first bone, in a state where a relative position of a wave transmitting and receiving surface to the cartilage is fixed, the ultrasonic waves being transmitted and received at the wave transmitting and receiving surface. The device includes an ultrasonic receiver configured to receive echo signals caused by the ultrasonic waves transmitted by the ultrasonic transmitter, a degeneration degree of the cartilage being diagnosed based on the echo signals received by the ultrasonic receiver, the ultrasonic receiver receiving the echo signals corresponding to a plurality of frames defined in a depth direction of the cartilage and a direction perpendicular to the depth direction, in each of the plurality of bent states. The device includes a low-frequency component extracting module configured to extract, in a frame direction that is an array direction of the plurality of frames, low-frequency echo data from the echo signals received by the ultrasonic receiver, the low-frequency echo data being echo data of a frequency component below a given frequency, and a deriving module configured to derive information of the cartilage based on the low-frequency echo data extracted by the low-frequency component extracting module.

(2) A bending operation may be performed on the second bone at a given cycle between first and second bent states where the bent angle is at a largest angle and a smallest angle among the plurality of bent states, respectively. The ultrasonic transmitter may transmit the ultrasonic waves at a given time interval.

(3) Further, the given frequency may be set to be below a frequency expressed as an inverse number of the given cycle.

(4) The deriving module may have an echo image generating module configured to generate an echo image as the information of the cartilage, based on the low-frequency echo data.

(5) The low-frequency component extracting module may include a Fourier transform module configured to Fourier transform, at least in the frame direction, three-dimensional echo data configured by arraying the echo data of every frame in the frame direction, and defined in the frame direction, the depth direction of the cartilage, and a direction perpendicular to both the frame and depth directions, and a low pass filter module configured to extract the low-frequency echo data from the three-dimensional echo data Fourier transformed by the Fourier transform module.

(6) Further, the Fourier transform module may three-dimensionally Fourier transform the three-dimensional echo data. The deriving module may include a selecting module configured to select low-frequency two-dimensional echo data from the three-dimensional echo data Fourier transformed by the Fourier transform module, the low-frequency two-dimensional echo data being two-dimensional echo data at low frequency in the frame direction, a spectral angular characteristic calculating module configured to calculate total values of echo intensities in regions as a spectral angular characteristic, the regions corresponding to a plurality of angular positions, respectively, set with respect to a reference line passing through an origin of the low-frequency two-dimensional echo data selected by the selecting module, and an angular width calculating module configured to calculate a width of an angle at which the total value becomes a given ratio with respect to a peak value of the spectral angular characteristic calculated by the spectral angular characteristic calculating module.

(7) The ultrasonic diagnosing device may further include an analysis region designing module configured to design, in one of the echo data of every frame, an analysis region that is a region defined in the depth direction of the cartilage and the direction perpendicular to the depth direction, including the cartilage, and excluding a subchondral bone to which the cartilage is attached. The selecting module may select the low-frequency two-dimensional echo data in the analysis region designed by the analysis region designing module.

(8) The ultrasonic diagnosing device may be used on a thigh bone as the first bone, and a shin bone as the second bone.

(9) Further, the wave transmitting and receiving surface may be disposed so that a normal direction thereof is oriented toward the cartilage and parallel to an extending direction of the thigh bone.

(10) The ultrasonic diagnosing device may further include a display unit configured to display the information of the cartilage derived by the deriving module.

(11) In order to solve the subject described above, a method of ultrasonic diagnosis according to another aspect of this disclosure, includes transmitting ultrasonic waves to a cartilage on an end part of a first bone through a soft tissue covering a joint including the end part of the first bone and an end part of a second bone, the transmitting the ultrasonic waves transmitting the ultrasonic waves to the cartilage in a plurality of bent states with different bent angles of the second bone with respect to the first bone, in a state where a relative position of a wave transmitting and receiving surface to the cartilage is fixed, the ultrasonic waves being transmitted and received at the wave transmitting and receiving surface. The method includes receiving echo signals caused by the ultrasonic waves transmitted by the transmitting the ultrasonic waves, a degeneration degree of the cartilage being diagnosed based on the echo signals received by the receiving the echo signals, the receiving the echo signals receiving the echo signals corresponding to a plurality of frames defined in a depth direction of the cartilage and a direction perpendicular to the depth direction, in each of the plurality of bent states. The method includes extracting, in a frame direction that is an array direction of the plurality of frames, low-frequency echo data, the low-frequency echo data being echo data of a frequency component below a given frequency, and deriving information of the cartilage based on the low-frequency echo data.

Effects of the Disclosure

According to this disclosure, a shape of a cartilage can accurately be detected and information of the cartilage can be derived based on echoes from the cartilage detected with high accuracy.

BRIEF DESCRIPTION OF DRAWINGS

FIGS. 2(A) and 2(B) show schematic views illustrating a knee joint when an ultrasonic wave is transmitted, in which FIG. 2(A) is a view illustrating a state where an angle (bent angle) between a thigh bone and a shin bone when the device is used is at a largest angle (first bent state), and FIG. 2(B) is a view illustrating a state where the bent angle is at a smallest angle (second bent state).

FIGS. 11(A) and 11(B) show echo images of the cartilage, in which FIG. 11(A) is one example of an echo image of a normal cartilage and FIG. 11(B) is one example of an echo image of a degenerated cartilage.

MODES FOR CARRYING OUT THE DISCLOSURE

Figure 1:
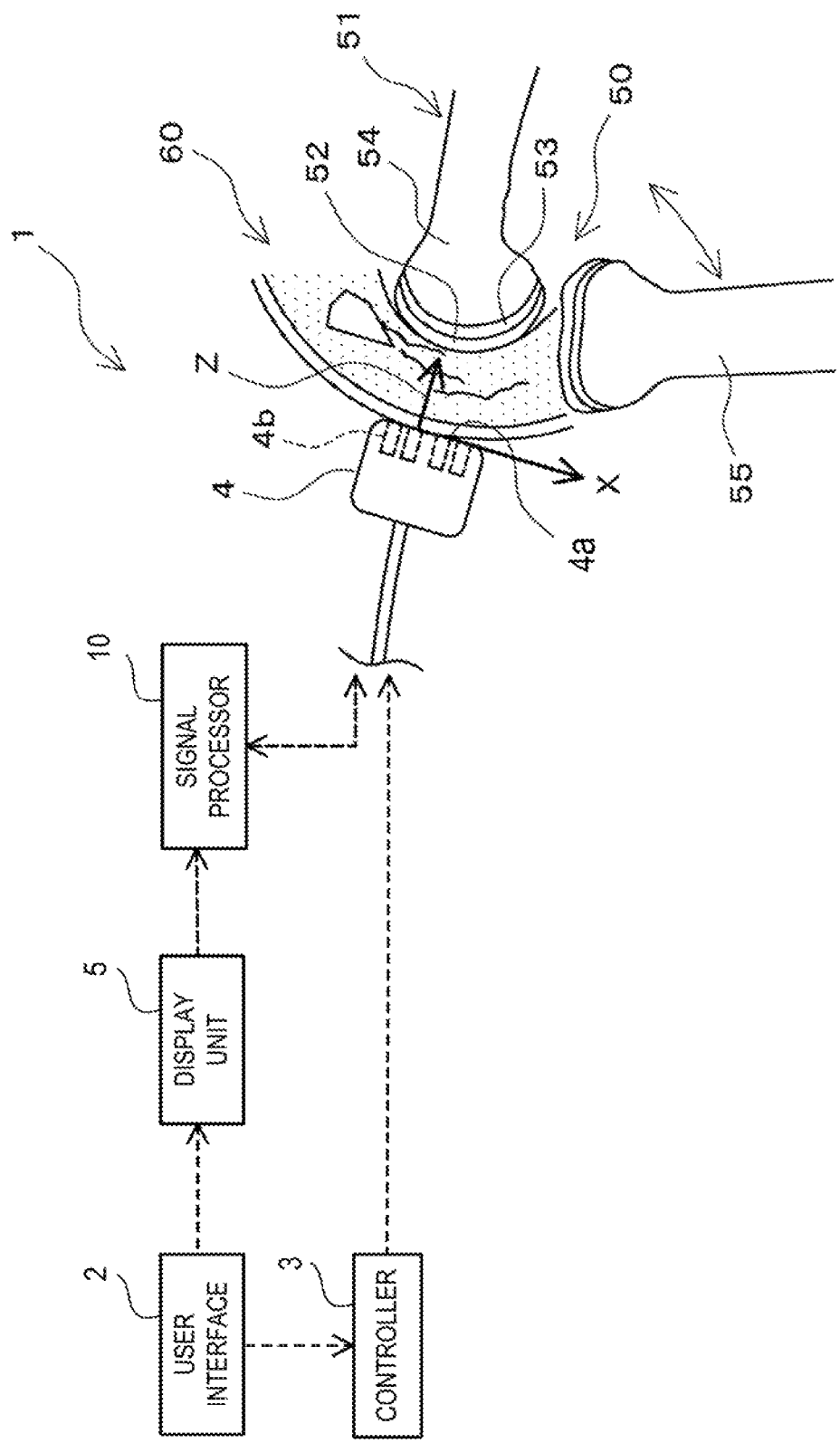
FIG. 1 shows a block diagram illustrating a configuration of an ultrasonic diagnosing device according to one embodiment of this disclosure, and a cross-sectional view schematically illustrating a knee of a patient in a state where a probe of the ultrasonic diagnosing device is installed thereon.

An ultrasonic diagnosing device 1 according to one embodiment of this disclosure is described with reference to the drawings. FIG. 1 is a schematic view of the ultrasonic diagnosing device 1 according to the embodiment of this disclosure. The ultrasonic diagnosing device 1 is used to diagnose a state (degeneration degree) of a cartilage near a proximal end of a thigh bone (first bone) in a knee of a patient. Specifically, the ultrasonic diagnosing device 1 calculates an index indicating the degeneration degree of the knee cartilage described above, for which further detailed description is given later. A user (e.g., doctor) can diagnose the knee cartilage of the patient based on the index.

Overall Configuration

As illustrated in FIG. 1, the ultrasonic diagnosing device 1 includes a user interface 2, a controller 3, a probe 4, a signal processor 10, and a display unit 5.

The user interface 2 is, for example, comprised of one of a keyboard and a touch panel, and receives an operational input from the user. In response to the operational input from the user, the user interface 2 commands the controller 3 to start a detection of a cartilage front surface. Further, the user interface 2 outputs, to the display unit 5, a command to set or switch a display mode in response to the operational input from the user. Note that, the user interface 2 may be incorporated with the display unit 5.

The controller 3 generates pulse-shaped ultrasonic signals and controls the probe 4 to transmit the ultrasonic signals therefrom.

The probe 4 includes a plurality of oscillators 4b arrayed in a direction parallel to a wave transmitting and receiving surface 4a (see FIG. 1). This array direction of the oscillators 4b becomes a scanning direction (an X-direction of FIG. 1, which is perpendicular to a depth direction of the cartilage 52). Each oscillator 4b is provided as an ultrasonic transmitter configured to transmit the ultrasonic signal toward the cartilage 52 at a given time interval. Further, the oscillator 4b is provided as an ultrasonic receiver configured to receive an echo signal of the transmitted ultrasonic signal.

As illustrated in FIG. 1, the probe 4 is made in contact with a soft tissue 60 of the knee such that a normal direction of the wave transmitting and receiving surface 4a of the probe 4 is oriented toward the cartilage 52 of the thigh bone 51 and also oriented from the proximal side to the distal side of the thigh bone 51 (i.e., parallel to an extending direction of the thigh bone 51). Thus, the ultrasonic waves are transmitted in the depth direction of the cartilage 52. Here, as illustrated in FIG. 1, the soft tissue 60 is a part existing on a front surface side of the knee with respect to the cartilage 52 of the thigh bone 51, and includes skin, muscles, etc. The cartilage 52 is attached to a subchondral bone 53. The subchondral bone 53 is a tissue coupled to a cancellous bone 54.

Figure 2A:
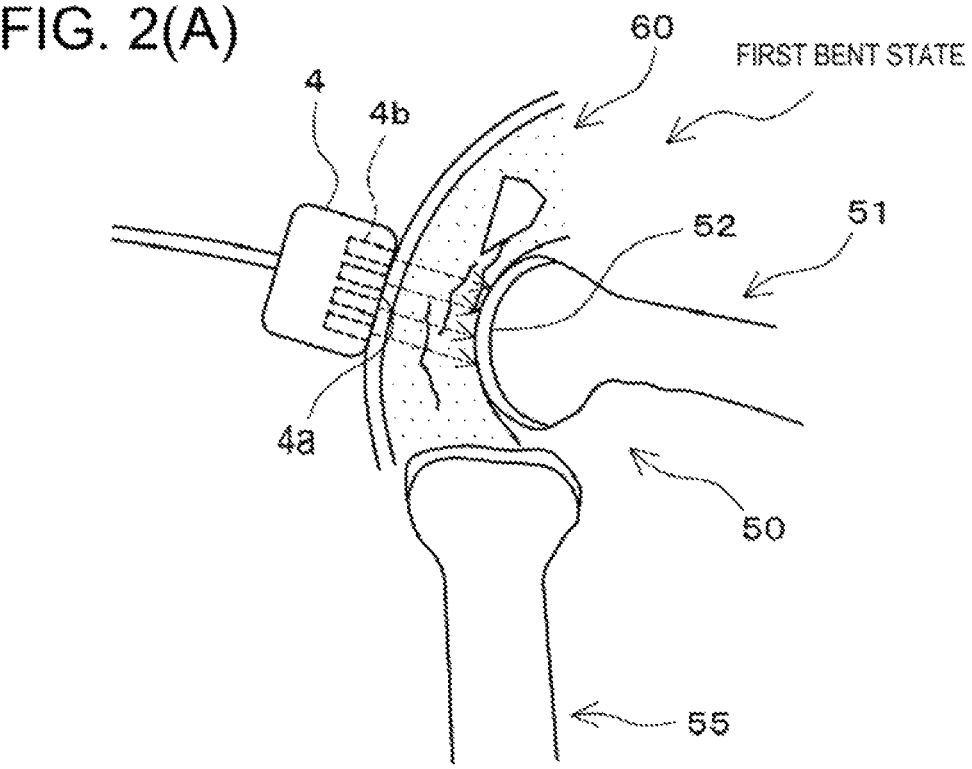
Figure 2B:
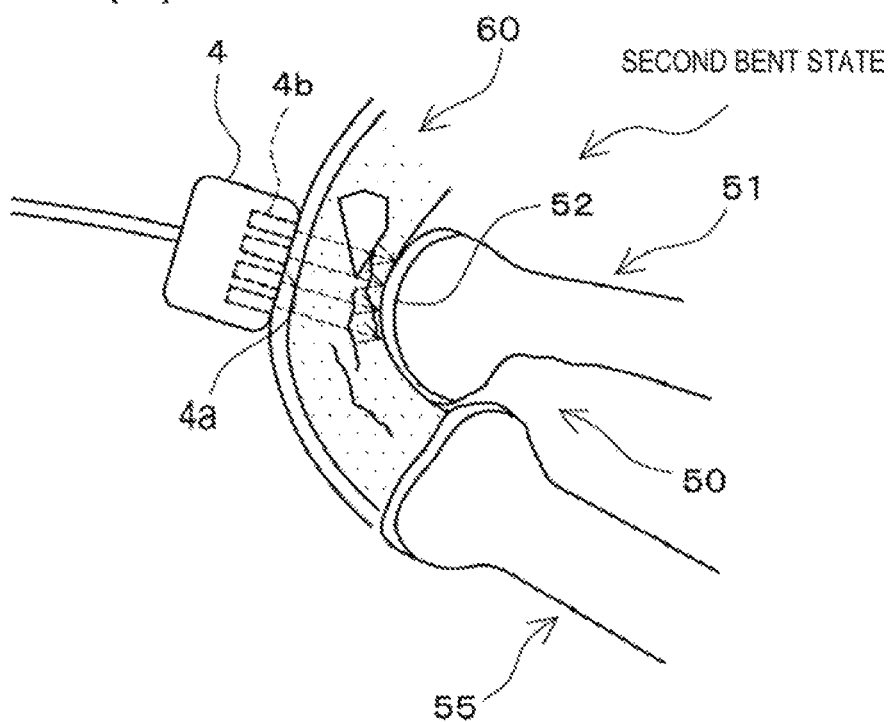

FIGS. 2(A) and 2(B) show schematic views illustrating a state of a knee joint 50 when the ultrasonic waves are transmitted. As illustrated in FIGS. 2(A) and 2(B), with the ultrasonic diagnosing device 1, in a plurality of bent states with different bent angles of a shin bone 55 (second bone) with respect to the thigh bone 51, the ultrasonic waves are transmitted from the respective oscillators 4b and reflection waves of the transmitted ultrasonic waves are received by the oscillators 4b. The echo signals obtained in each bent state are outputted to the signal processor 10.

In this embodiment, as one example, each oscillator 4b transmits the ultrasonic wave at the given time interval while the doctor moves a lower part of the knee (hereinafter, may be referred to as the under-knee part) to bend and stretch the knee of a leg of the patient at a given cycle. Specifically, the doctor performs the bending and stretching by moving the under-knee part of the patient so that the state of the knee of the patient is repeatedly changed between a first bent state illustrated in FIG. 2(A) and a second bent state illustrated in FIG. 2(B) at the given cycle (e.g., 10 seconds). During this time, the oscillator 4b transmits the ultrasonic wave at a certain time interval and receives an echo signal of the ultrasonic wave transmitted in each bent state between the first and second bent states.

While performing the bending and stretching by moving the under-knee part of the patient as described above, a relative position of the probe 4 to the thigh bone 51 is fixed. Thus, while performing the bending and stretching of the knee, a position of the cartilage 52 against the probe 4 is substantially the same, whereas a position of the soft tissue 60 against the probe 4 changes at a given periodicity (the given cycle).

The signal processor 10 analyzes a state of the cartilage 52 based on the echo signals received by the oscillators 4b as described above, and outputs the analysis result to the display unit 5. A specific configuration and operation of the signal processor 10 are described later in detail.

The display unit 5 displays the analysis result of the cartilage 52 obtained by the signal processor 10. Specifically, the display unit 5 displays an echo image indicating a shape of the cartilage 52. Further, the display unit 5 displays a characteristic amount as an index indicating the state of the cartilage, which is calculated by the signal processor 10. The user diagnoses the state of the cartilage 52 of the knee of the patient based on these echo image and characteristic amount.

Configuration of Signal Proccessor

Figure 3:
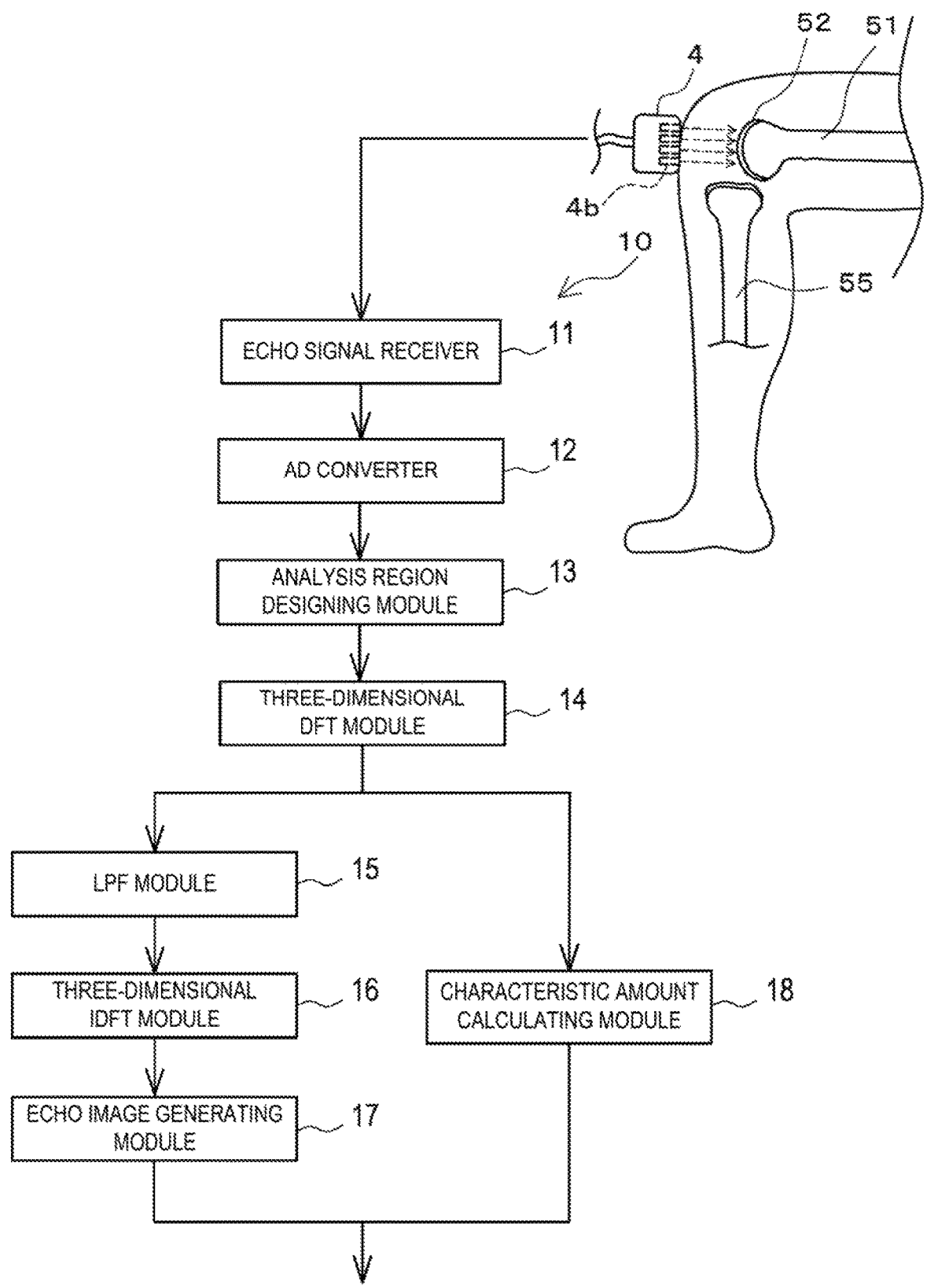
FIG. 3 is a block diagram illustrating a configuration of a signal processor of the ultrasonic diagnosing device illustrated in FIG. 1.

FIG. 3 is a block diagram illustrating a configuration of the signal processor 10 of the ultrasonic diagnosing device 1 according to this embodiment. As illustrated in FIG. 3, the signal processor 10 includes an echo signal receiver 11, an AD converter 12, an analysis region designing module 13, a three-dimensional DFT module 14, an LPF module 15, a three-dimensional IDFT module 16, an echo image generating module 17, and a characteristic amount calculating module 18. The signal processor 10 is comprised of hardware including a CPU, a RAM and a ROM (not illustrated). Further, the signal processor 10 is configured by using software including a signal processing program stored in the ROM.

The signal processing program is a program that causes the signal processor 10 to implement a signal processing method according to one embodiment of this disclosure. This program may be installed externally. This program installed is distributed while stored in a recording medium, for example. The hardware and the software are configured to operate in cooperation with each other, which as a result enables the signal processor 10 to function as the echo signal receiver 11, the AD converter 12, the analysis region designing module 13, etc., which are described above.

The echo signal receiver 11 performs a given amplification on each of the echo signals obtained in the respective bent states described with reference to FIGS. 2(A) and 2(B), and outputs it to the AD converter 12.

The AD converter 12 samples the echo signal at a given time interval to discretize data. The echo signals sampled to be the discretized data become echo data. Thus, a plurality of sheets (corresponding to a plurality of frames) of two-dimensional echo data defined in the scanning direction X and the depth direction Z can be obtained. In other words, the AD converter 12 can obtain three-dimensional echo data. The AD converter 12 outputs the echo data to the analysis region designing module 13.

Figure 4:
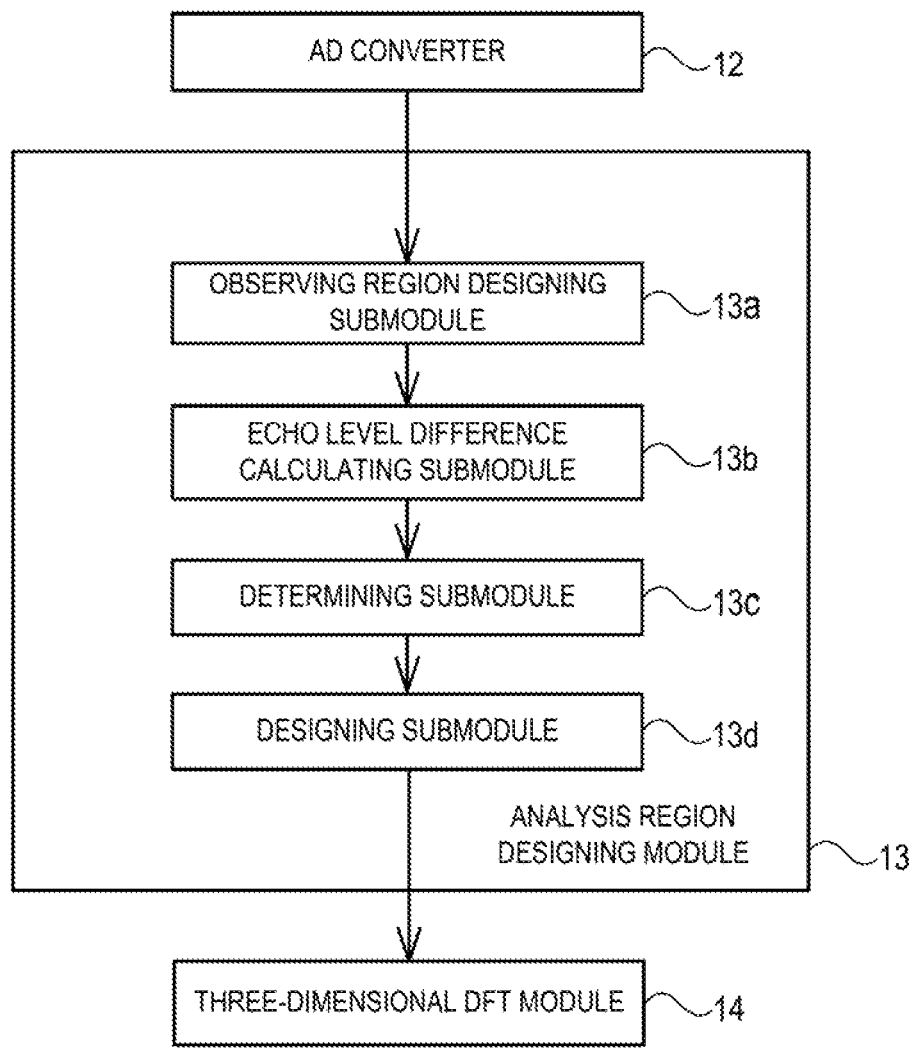
FIG. 4 is a block diagram illustrating one example of a configuration of an analysis region designing module illustrated in FIG. 3.

FIG. 4 is a block diagram illustrating one example of a configuration of the analysis region designing module 13. The analysis region designing module 13 designs a region which does not include echo signals from the subchondral bone 53 unnecessary in diagnosing the state of the cartilage 52, to be an analysis region. As illustrated in FIG. 4, the analysis region designing module 13 has an observing region designing submodule 13a, an echo level difference calculating submodule 13b, a determining submodule 13c, and a designing submodule 13d.

Figure 5:
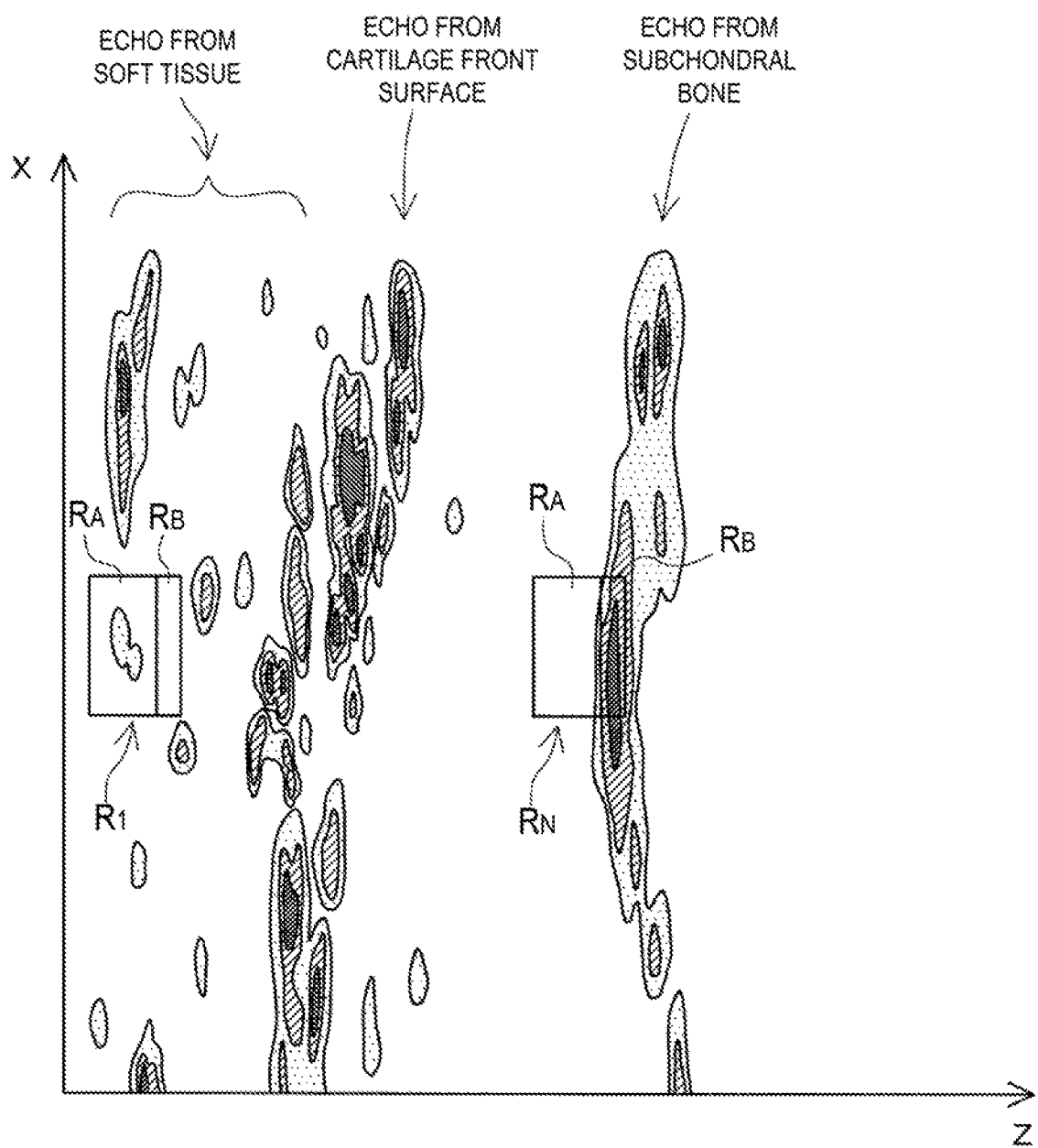
FIG. 5 is a view of an echo image based on echo data outputted by an AD converter, illustrating designing of an observing region.

FIG. 5 is a view of an echo image based on the echo data outputted by the AD converter 12, illustrating designing of an observing region. The view of FIG. 5 is illustrated as an echo image of a region defined in the scanning direction of the probe 4 (X-direction of FIG. 5) and the depth direction of the cartilage (Z-direction of FIG. 5).

As illustrated in FIG. 5, the observing region designing submodule 13a designs a rectangular area longer in the scanning direction (X-direction) to be an observing region $R_n$ (n=1, 2, ..., N). The observing region $R_n$ is formed by a first region $R_A$ and a second region $R_B$. The first region $R_A$ is a part of the observing region $R_n$ on the knee front surface side. The second region $R_B$ is a part of the observing region $R_n$ located on the deeper side of the first region $R_A$ in the depth direction (Z-direction) and is narrower than the first region $R_A$ in the depth direction. The observing region designing submodule 13a designs the observing region $R_n$ a plurality of times while shifting it to the deeper side by a given interval at a time.

The echo level difference calculating submodule 13b calculates an average value of echo intensities of all the samples in the first region (first average value) and an average value of echo intensities of all the samples in the second region (second average value), and calculates a subtraction value by subtracting the second average value from the first average value. The echo level difference calculating submodule 13b calculates the subtraction value for each of the plurality of designed observing regions $R_n$.

The determining submodule 13c selects a lowest subtraction value from the plurality of subtraction values calculated for the plurality of designed observing regions $R_n$, and determines the observing region $R_N$ for which the lowest subtraction value is calculated, as a subchondral bone region which is a region including the subchondral bone.

The designing submodule 13d designs, as the analysis region, a region excluding the subchondral bone region determined by the determining submodule 13c, specifically, a rectangular region located on the shallower side of the subchondral bone region.

The three-dimensional DFT module 14 (Fourier transform module) performs three-dimensional DFT (Discrete Fourier Transform) on the echo data in the analysis region designed by the analysis region designing module 13. Thus, the three-dimensional echo data including data in a real space domain and a time domain can be converted into three-dimensional echo data including data in a wavenumber space domain and a frequency domain. The three-dimensional echo data is outputted to the LPF module 15 and the characteristic amount calculating module 18.

The LPF module 15 (low pass filter module) performs LPF (Low Pass Filtering) on the three-dimensional echo data outputted by the three-dimensional DFT module 14, in the frame direction. Thus, data at high frequency (echoes of the soft tissue 60 which changes in position by bending the knee) can be removed from the echo data at low frequency (echoes of the cartilage 52 which substantially does not change in position by bending the knee). In this embodiment, a cutoff frequency is set to be below a frequency expressed as an inverse number of the given cycle at which the bending and stretching of the knee is performed (e.g., 0.1 Hz), and frequency components above the cutoff frequency are cut off. Thus, the echo signals of the soft tissue 60 having substantially the same cycle as the given cycle can be removed from the echo signals of the cartilage 52 having a sufficiently shorter cycle than the given cycle. The data obtained by the LPF module 15 is outputted to the three-dimensional IDFT module 16 as the low-frequency echo data. The low-frequency echo data can be displayed as a power spectrum on coordinates defined by a wavenumber $k_X$ in the X-direction and a wavenumber $k_Z$ in the Z-direction.

The three-dimensional IDFT module 16 inverse Fourier transforms the low-frequency echo data outputted by the LPF module 15. Thus, the three-dimensional IDFT module 16 transforms the low-frequency echo data, which is the data in the wavenumber space domain and the frequency domain, into echo data in the real space.

Note that, the three-dimensional DFT module 14, the LPF module 15, the three-dimensional IDFT module 16, which are described above, function as a low-frequency component extracting module configured to extract, from the three-dimensional echo data outputted by the AD converter 12, low-frequency echo data which is echo data of frequency components below a given frequency.

Figure 6:
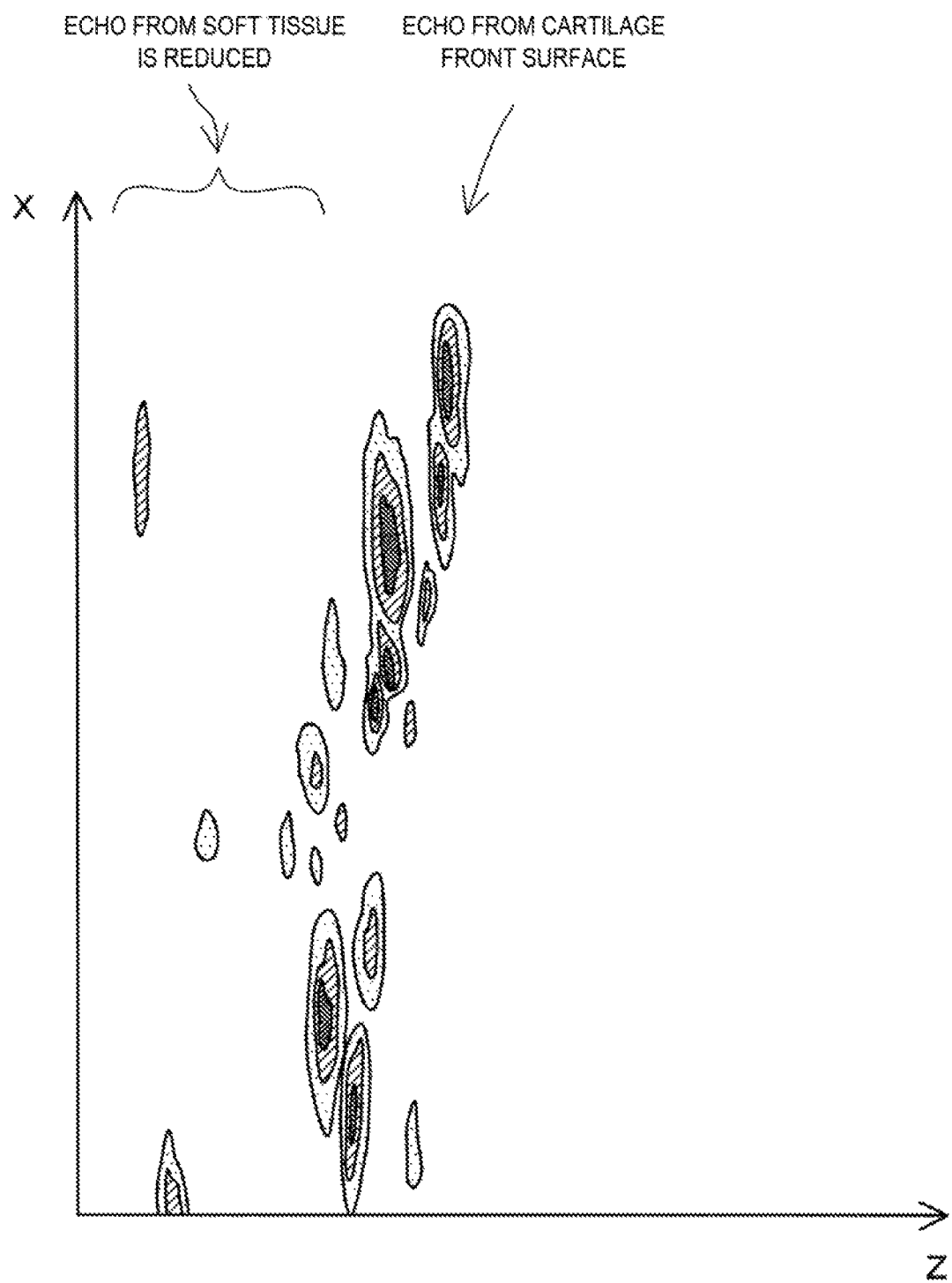
FIG. 6 is a view illustrating one example of an echo image generated by an echo image generating module.

FIG. 6 is a view illustrating one example of the echo image generated by the echo image generating module 17. The echo image generating module 17 generates the echo image based on the echo data which is generated by the three-dimensional IDFT module 16 and from which the echo data of the soft tissue 60 is reduced. The echo image generating module 17 of this embodiment generates an echo level image based on the echo data obtained from positions in the analysis region designed by the analysis region designing module 13. The echo level image is configured with a plurality of pixels arrayed in a grid form. Each pixel is disposed at a position on a display screen in association with a corresponding position in the analysis region, and has a luminance level corresponding to an echo intensity at the corresponding position in the analysis region. In this embodiment, for example, the luminance level is displayed in association with a color tone which gradually changes in an order of red, orange, yellow, green, blue, and dark blue, as the luminance level changes from high to low. Note that in FIG. 6, for the sake of convenience, a region with a high luminance level is hatched with high density and a region with a low luminance level is hatched with low density. The echo image is displayed on the display unit 5.

Figure 7:
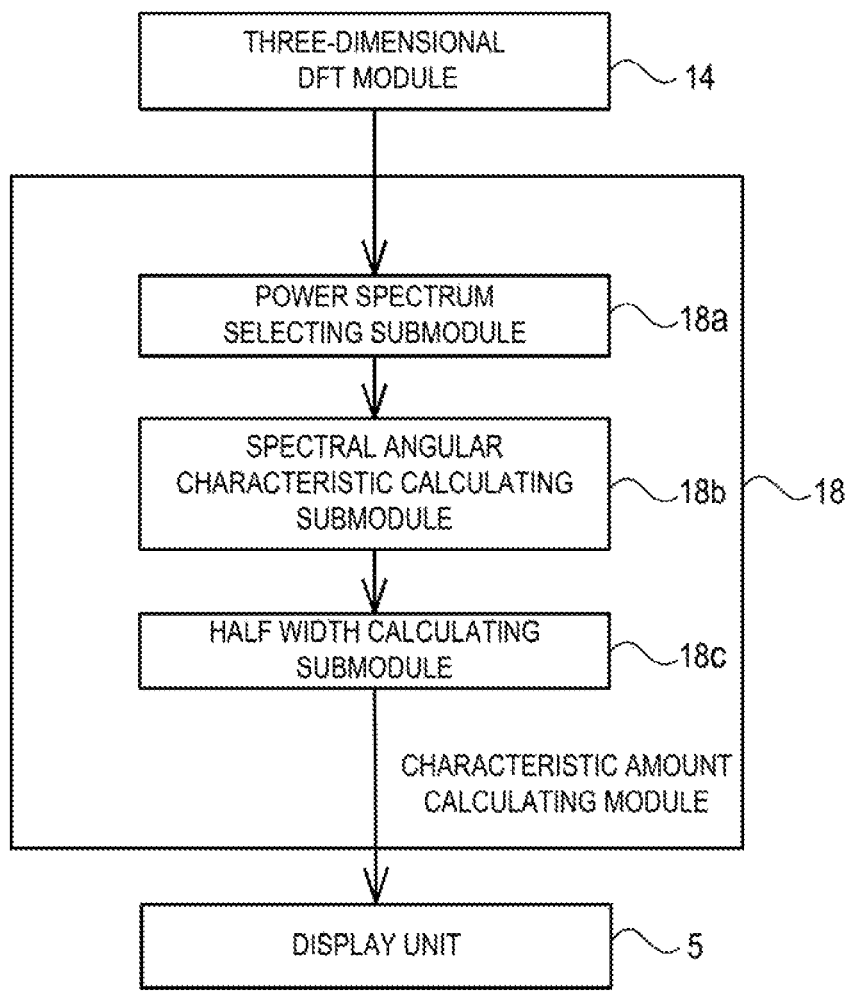
FIG. 7 is a block diagram illustrating a configuration of a characteristic amount calculating module illustrated in FIG. 3.

FIG. 7 is a block diagram illustrating a configuration of the characteristic amount calculating module. Based on the low-frequency echo data outputted by the LPF module 15, in other words, echo data mainly configured by the echo data from the cartilage 52, the characteristic amount calculating module 18 calculates the characteristic amount which is the index indicating a characteristic of the echo data. In this embodiment, as the characteristic amount, the characteristic amount calculating module 18 calculates a half width described later in detail.

As illustrated in FIG. 7, the characteristic amount calculating module 18 includes a power spectrum selecting submodule 18a, a spectral angular characteristic calculating submodule 18b, and a half width calculating submodule 18c (angular width calculating module).

Figure 8:
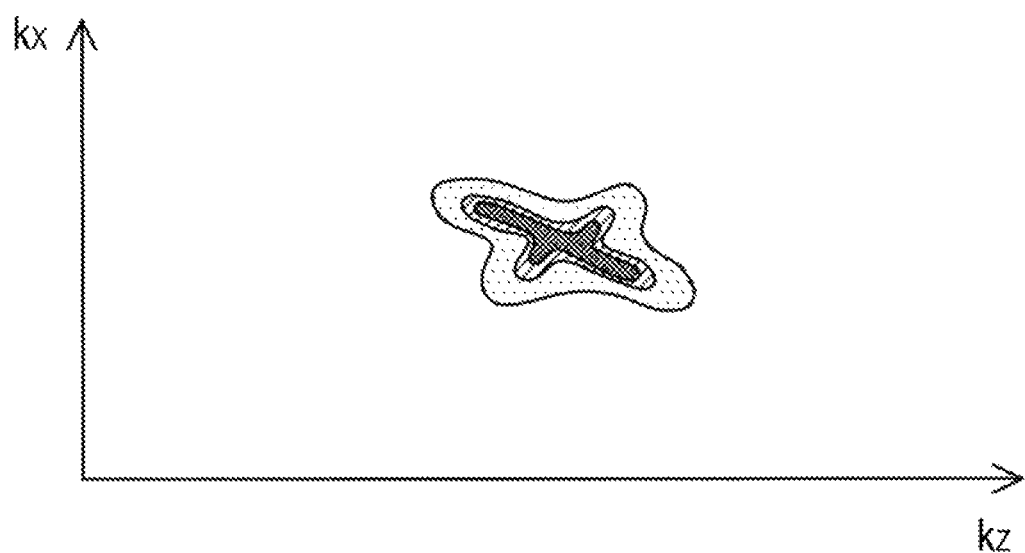
FIG. 8 is a view illustrating a power spectrum of low-frequency components selected from a power spectrum $S^2$ obtained from three-dimensional echo data outputted by a three-dimensional DFT module.

FIG. 8 is a view illustrating a power spectrum of the low-frequency components. The power spectrum selecting submodule 18a selects the power spectrum of the low-frequency components from a power spectrum obtained based on the three-dimensional echo data outputted by the three-dimensional DFT module 14. In other words, the power spectrum selecting submodule 18a selects the power spectrum mainly configured by the echo data of the cartilage 52.

Figure 9:
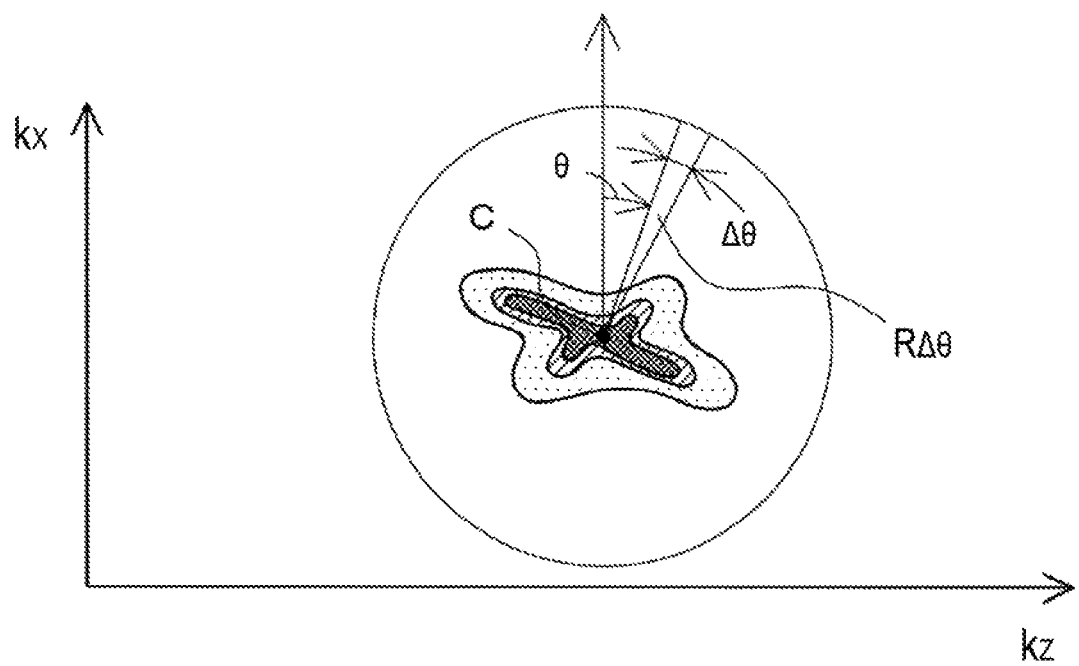
FIG. 9 is a view illustrating a method of calculating a spectral angular characteristic based on the power spectrum illustrated in FIG. 8.
Figure 10:
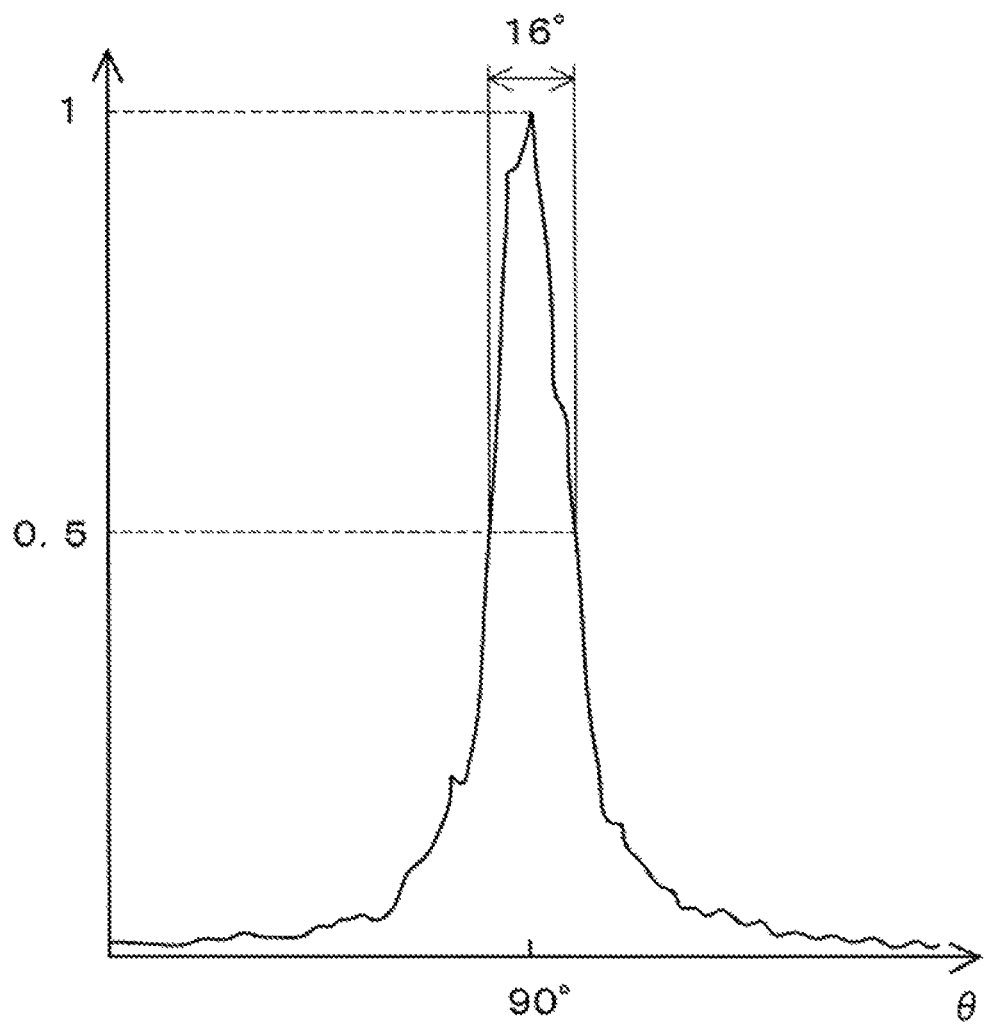
FIG. 10 is a waveform illustrating one example of the spectral angular characteristic obtained by the method illustrated in FIG. 9.

FIG. 9 is a view illustrating a method of calculating a spectral angular characteristic based on the power spectrum illustrated in FIG. 8. FIG. 10 is a waveform illustrating one example of the spectral angular characteristic obtained by the method illustrated in FIG. 9. As illustrated in FIG. 9, the spectral angular characteristic calculating submodule 18b designs a target region $R_{A\theta}$ that is a fan-shaped micro region centering on a center position C (origin) of the power spectrum.

The spectral angular characteristic calculating submodule 18b shifts a rotational position θ of the target region $R_{A\theta}$ within a range of 0 to 180 degrees. In each target region $R_{A\theta}$ which gradually shifts in its rotational position θ, the spectral angular characteristic calculating submodule 18b adds echo intensities of all locations. The spectral angular characteristic calculating submodule 18b calculates the spectral angular characteristic illustrated in FIG. 10, by calculating the total values of the echo intensities corresponding to the respective rotational positions θ as described above. Note that, although the total values of the echo intensities corresponding to the respective rotational positions θ are standardized in FIG. 10, without limiting to this, the total values described above may be used as they are.

The half width calculating submodule 18c calculates the half width of a peak of the spectral angular characteristic calculated by the spectral angular characteristic calculating submodule 18b. Specifically, the half width calculating submodule 18c detects the peak value within a given angle range near 90 degrees (e.g., 80 to 100 degrees), and calculates a half width of a peak waveform having the peak value (in the example illustrated in FIG. 10, 16 degrees). The half width is outputted to the display unit 5 as the characteristic amount which is the index indicating the degeneration degree of the cartilage 52, and displayed thereon. Note that in this embodiment, the half width is obtained based on the spectral angular characteristic; however, it is not limited to this. Specifically, in the spectral angular characteristic, a width of an angle in which the total value becomes a given ratio with respect to the peak value of the spectral angular characteristic may be calculated.

About Half Width

Next, a relationship between the half width calculated as described above and the degeneration degree of the cartilage 52 is described.

Figure 11B:
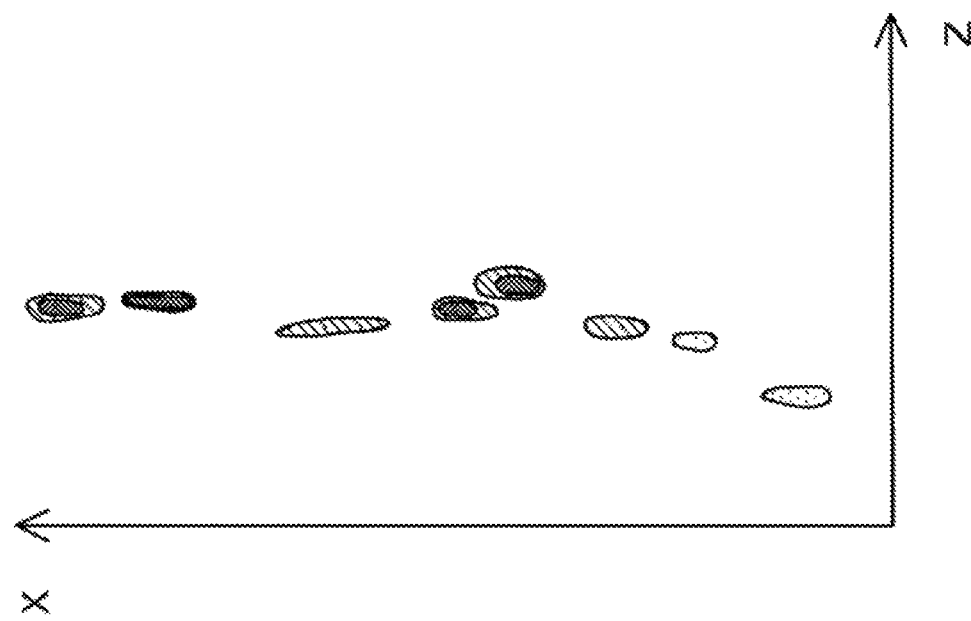
Figure 11A:
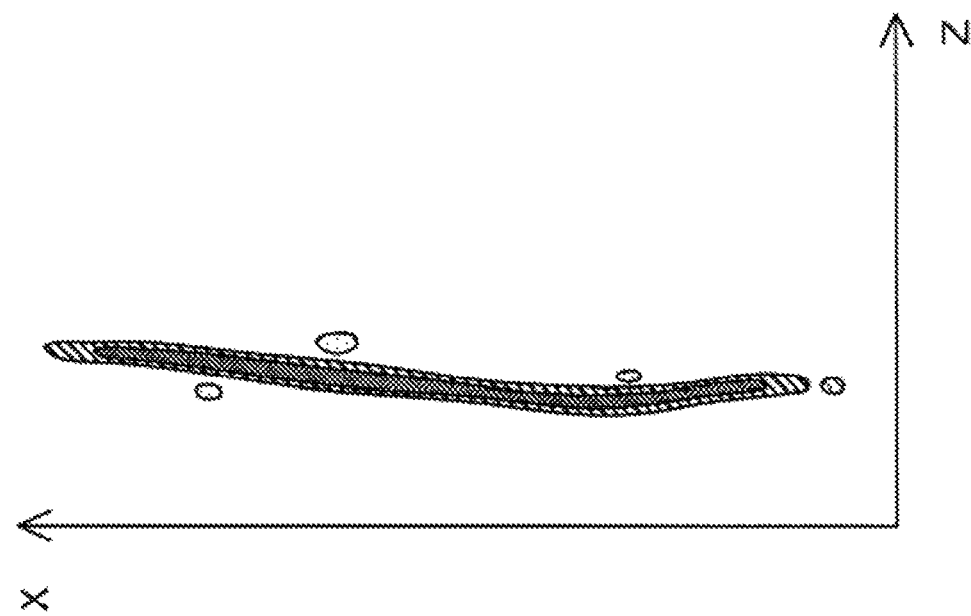
Figure 12:
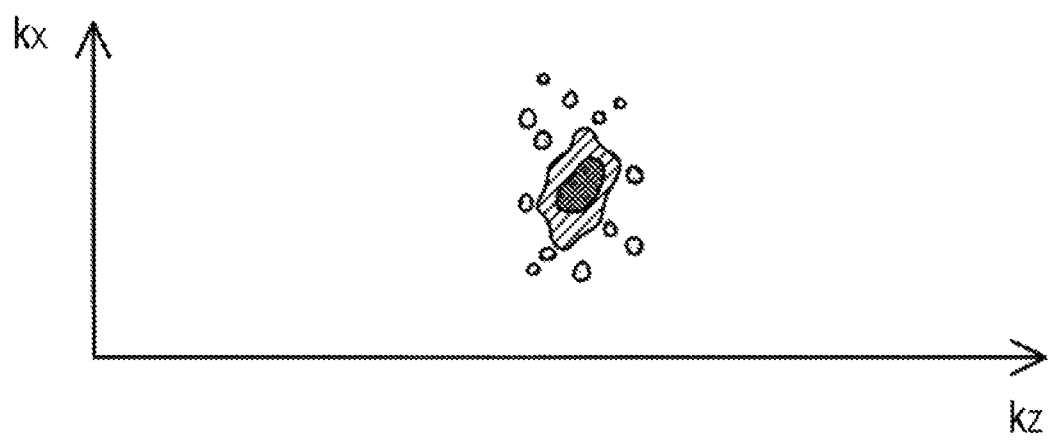
FIG. 12 is an image of the echo data obtained by inverse Fourier transforming the echo data of the degenerated cartilage illustrated in FIG. 11(B).

FIGS. 11(A) and 11(B) show echo images of the cartilage, in which FIG. 11(A) is one example of an echo image of a normal cartilage and FIG. 11(B) is one example of an echo image of a degenerated cartilage. Further, FIG. 12 is an image of the echo data obtained by inverse Fourier transforming the echo data of the degenerated cartilage illustrated in FIG. 11(B). Note that, the echo image of the cartilage illustrated in FIG. 11(A) is obtained by inverse Fourier transforming the echo data illustrated in FIG. 8.

As illustrated in FIG. 11(A), the echo image of the normal cartilage continues in the scanning direction X of the probe 4. Therefore, by inverse Fourier transforming the data of this echo image, a power spectrum having a directivity is generated (see FIG. 8). Thus, the half width of the spectral angular characteristic calculated based on this power spectrum becomes comparatively narrow as illustrated in FIG. 10.

Figure 13:
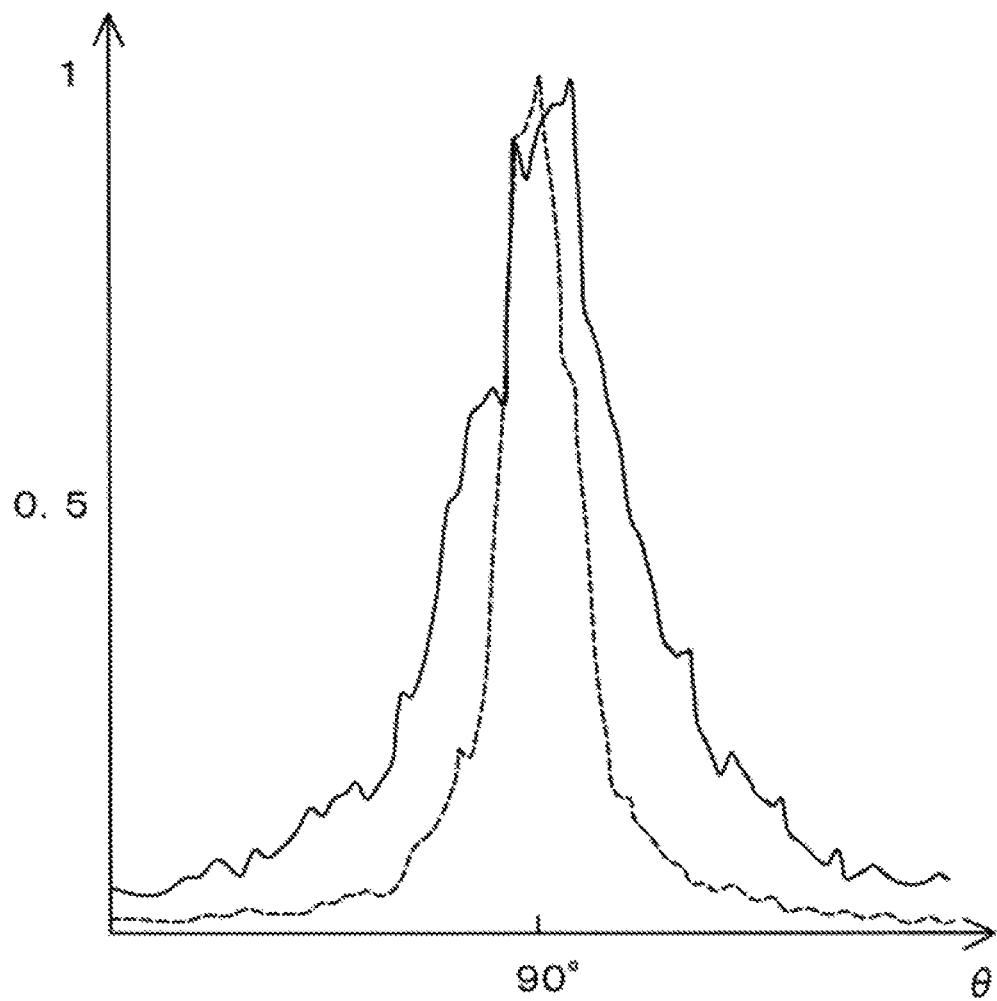
FIG. 13 is a view illustrating a waveform indicating the spectral angular characteristic of the normal cartilage and a waveform indicating the spectral angular characteristic of the degenerated cartilage in an overlapped manner, illustrating a difference therebetween.

On the other hand, the echo image of the degenerated cartilage is discrete in the scanning direction X of the probe 4 as illustrated in FIG. 11(B), unlike the echo image of the normal cartilage illustrated in FIG. 11(A). Therefore, by inverse Fourier transforming the data of this echo image, a power spectrum having a comparatively narrow directivity is generated (see FIG. 12). Thus, as illustrated in FIG. 13, the half width of the spectral angular characteristic calculated based on this power spectrum becomes comparatively wider than the half width of the spectral angular characteristic obtained from the normal cartilage. Note that, in FIG. 13, the waveform indicated by a dashed line is the spectral angular characteristic obtained from the normal cartilage, and the waveform indicated by a solid line is the spectral angular characteristic obtained from the degenerated cartilage.

Operation of Signal Processor

Figure 14:
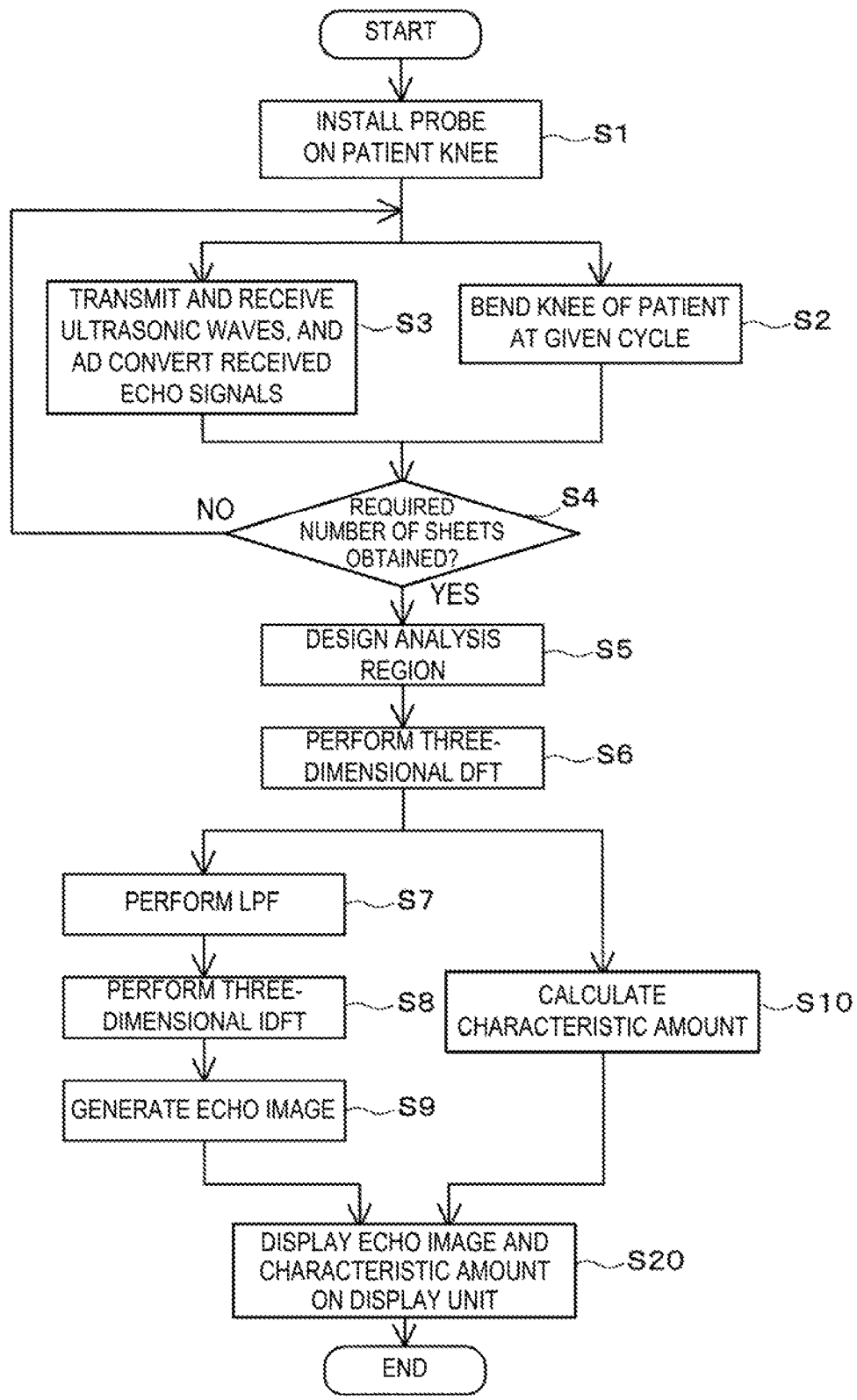
FIG. 14 is a flowchart illustrating operation of the ultrasonic diagnosing device.

FIG. 14 is a flowchart illustrating the operation of the signal processor 10. The operation of the signal processor 10 is described with reference to FIG. 14.

First at S1, the probe 4 is installed on the knee of the patient. Here, the probe 4 is installed on the knee of the patient so that the normal direction of the wave transmitting and receiving surface 4a is parallel to the extending direction of the thigh bone 51.

Next at S2, with reference to FIGS. 2(A) and 2(B), the knee of the patient is bent and stretched at the given cycle between the first and second bent states. The bending and stretching is performed by, for example, the doctor swinging the under-knee part of the patient.

On the other hand, parallel to S2, the transmission and reception of the ultrasonic wave are performed by the oscillators 4b of the probe 4 at S3. The echo signals received by the oscillators 4b are performed the given amplification by the echo signal receiver 11 and converted into digital signals by the AD converter 12.

Next at S4, whether the data required for the three-dimensional DFT performed later is acquired is determined. Specifically, whether echo data is obtained in a required number (e.g., 32) of bent states is determined. If the echo data is obtained in the required number of bent states (S4: YES), the operation proceeds to S5. On the other hand, the echo data is not obtained in the required number of bent states (S4: NO), the operation returns to S2 and S3, and the processes at S2 and S3 are performed again.

Next at S5, the analysis region is designed. Specifically, with reference to FIG. 5, the observing region designing submodule 13a designs an observing region $R_1$ formed by the first and second regions $R_A$ and $R_B$, and the echo level difference calculating submodule 13b calculates the average values of the echo intensities of all the samples in the respective regions $R_A$ and $R_B$ (first and second average values), and then calculates the subtraction value by subtracting the second average value from the first average value. At S5, the subtraction value is calculated for each observing region $R_n$ which is shifted in the depth direction by the given interval at a time. Then, the determining submodule 13c determines the observing region with the highest subtraction value, to be the subchondral bone region which is the region including the subchondral bone, and the designing submodule 13d designs the rectangular region on the shallower side of the subchondral bone region, to be the analysis region.

Next at S6, among the echo data of the knee joint corresponding to the plurality of bent states, the echo data in the analysis region designed at S5 is performed the three-dimensional DFT. Thus, the three-dimensional echo data including the data in the wavenumber space domain and the frequency domain can be obtained.

Next at S7, the LPF module 15 performs the LPF on the three-dimensional echo data in the frame direction, so as to generate low-frequency echo data. Thus, the echo signals from the soft tissue 60 can be reduced.

Next at S8, the three-dimensional IDFT module 16 inverse Fourier transforms the low-frequency echo data. Thus, the three-dimensional IDFT module 16 converts the low-frequency echo data, which is the data in the wavenumber space domain and the frequency domain, into echo data in the real space.

Next at S9, the echo image generating module 17 generates the echo image (see FIG. 6) based on the low-frequency echo data generated by the three-dimensional IDFT module 16 (i.e., echo data in which the echo signals of the soft tissue 60 are already reduced). This echo image is displayed on the display unit 5 as information of the cartilage.

Figure 15:
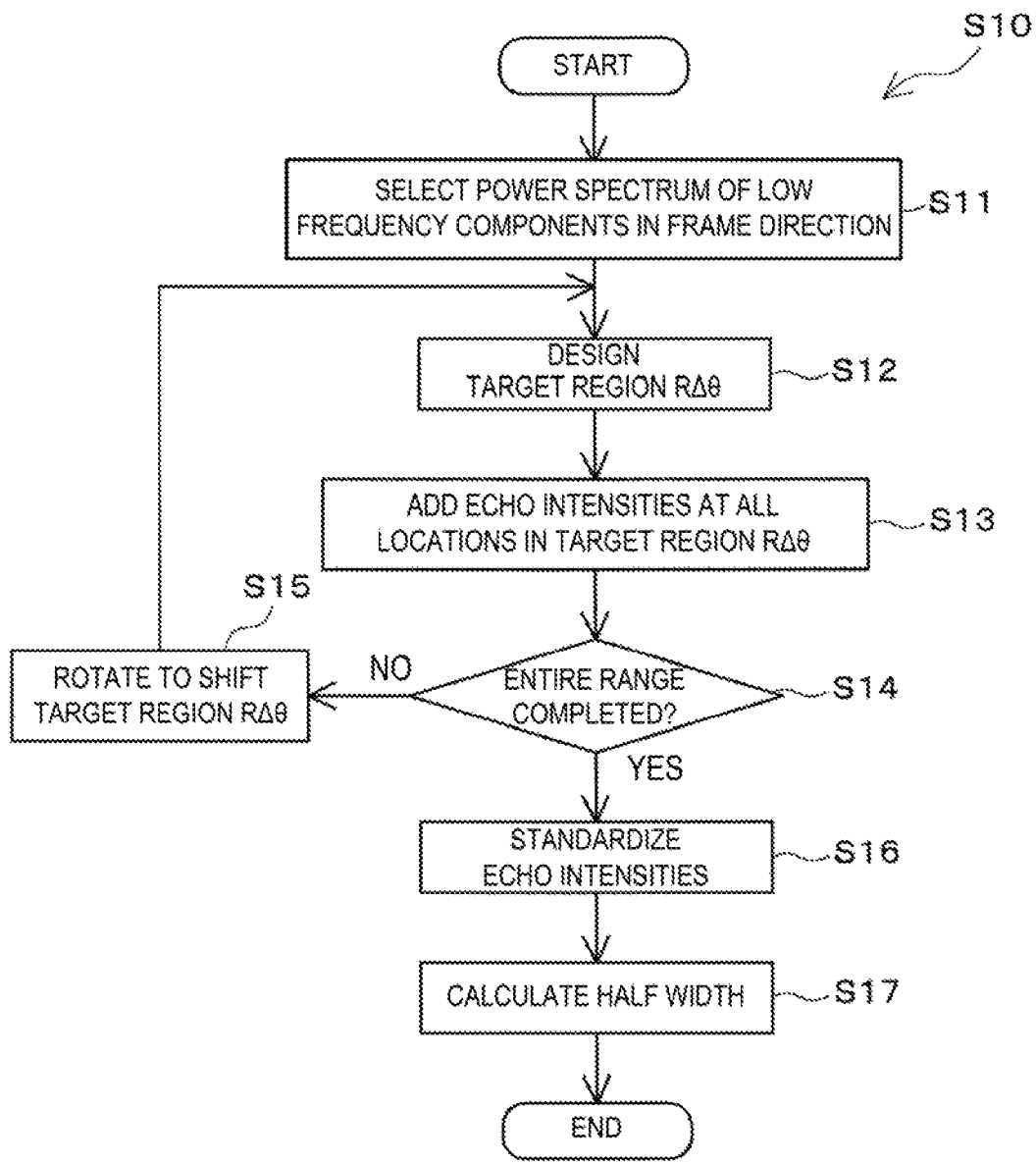
FIG. 15 is a flowchart illustrating respective processings performed at a step in which a characteristic amount is calculated.

On the other hand, at S10, the characteristic amount calculating module 18 calculates the half width as the characteristic amount. FIG. 15 is a flowchart illustrating respective processings performed at S10. The processings of calculating the characteristic amount are described with reference to FIG. 15.

First at S11, the power spectrum selecting submodule 18a selects the power spectrum of the low-frequency components, from the power spectrum obtained based on the three-dimensional echo data outputted by the three-dimensional DFT module 14. Note that, the power spectrum selecting submodule 18a may select the power spectrum of the low-frequency components from the power spectrum obtained based on the low frequency echo data generated by the LPF module 15.

Next at S12, the spectral angular characteristic calculating submodule 18b designs the target region $R_{\Delta\theta}$ that is the fan-shaped micro region centering on the center position C (origin) of the power spectrum (see FIG. 9). At S12, for example, the target region $R_{\Delta\theta}$ is designed so that the rotational angle becomes zero degree.

Next at S13, the spectral angular characteristic calculating submodule 18b calculates the total value of the echo intensities at all the locations in the target region $R_{\Delta\theta}$.

Next at S14, the spectral angular characteristic calculating submodule 18b determines whether the total value is calculated over the entire range of the region for which the total value is to be calculated in the selected power spectrum. Specifically, the spectral angular characteristic calculating submodule 18b determines whether the rotational angle of the target region $R_{\Delta\theta}$ has reached 180 degrees. If the rotational angle has not reached 180 degrees (S14: NO), at S15, the spectral angular characteristic calculating submodule 18b shifts the position of the target region $R_{\Delta\theta}$ by rotating the target region $R_{\Delta\theta}$ by the given angle, and the processing at S13 is performed again on the newly designed target region $R_{\Delta\theta}$. On the other hand, if the rotational angle has reached 180 degrees (S14: YES), the operation proceeds to S16.

Next at S16, the spectral angular characteristic calculating submodule 18b standardizes the total values calculated as described above. Specifically, the spectral angular characteristic calculating submodule 18b detects a highest value of the total values calculated for every rotational angle, calculates a coefficient with which the highest value becomes one (1) after standardization, and multiplies all of the total values by the coefficient. Thus, the spectral angular characteristic can be obtained. Note that, S16 may be omitted so that S17 is performed next to S14.

Finally at S17, the half width calculating submodule 18c obtains the half width of the spectral angular characteristic. The half width is displayed on the display unit 5 as the characteristic amount.

Effects

As described above, with the ultrasonic diagnosing device 1 of this embodiment, by transmitting the ultrasonic waves at a plurality of timings while the bent angle of the shin bone 55 with respect to the thigh bone 51 is changed in the state where the relative position of the probe 4 to the cartilage 52 is fixed, the echo signals of the cartilage 52 are obtained in each of the plurality of bent states. Further, by extracting the low-frequency components from the respective echo signals obtained in the plurality of bent states, the echoes caused by the soft tissue 60, which are high-frequency components, can be reduced. In other words, unnecessary echoes (in the case of this embodiment, the echoes from the soft tissue 60) can be removed from the desired echoes (in the case of this embodiment, the echoes from the cartilage 52). In this manner, even when the desired echoes and the unnecessary echoes have a small difference in echo level, the unnecessary echoes can surely be separated from the desired echoes.

Therefore, with the ultrasonic diagnosing device 1, the shape of the cartilage 52 can accurately be detected.

Moreover, with the ultrasonic diagnosing device 1, the information of the cartilage 52 (in the case of this embodiment, the echo image of the cartilage 52 and the half width which is the characteristic amount of the cartilage 52) can be derived based on the accurately detected shape of the cartilage 52. Therefore, the degeneration degree of the cartilage can be diagnosed at higher accuracy.

Moreover, with the ultrasonic diagnosing device 1, the ultrasonic waves are transmitted, at the give time interval, to the knee joint on which the bending and stretching is performed at the given cycle. Thus, the echo signals can smoothly be acquired in a comparatively short period of time.

Moreover, with the ultrasonic diagnosing device 1, the cutoff frequency is set to be below the cycle expressed as the inverse number of the given cycle at which the bending and stretching of the knee is performed (in the case of this embodiment, 0.1 Hz). Thus, the cutoff frequency can suitably be set.

Moreover, with the ultrasonic diagnosing device 1, the echo image is generated as the information of the cartilage. Thus, the user (e.g., doctor) can diagnose the state of the cartilage based on the echo image.

Moreover, with the ultrasonic diagnosing device 1, the three-dimensional echo data defined in the frame direction, the depth direction of the cartilage (Z-direction), and the direction (X-direction) perpendicular to the depth direction is Fourier transformed in the frame direction, and the high-frequency components are removed from the Fourier-transformed three-dimensional echo data, by the low pass filter module. Thus, the echo signals caused by the soft tissue 60 can suitably be removed from the three-dimensional echo data.

Moreover, with the ultrasonic diagnosing device 1, the three-dimensional echo data is Fourier transformed in all the directions, and the low-frequency components (low-frequency two-dimensional echo data) in the frame direction are extracted from the Fourier-transformed three-dimensional echo data, and the characteristic amount (half width) is calculated based on the extracted data. Thus, the removal of the unnecessary echoes (echoes from the soft tissue 60) and the derivation of the analysis result of the desired echoes (echoes from the cartilage 52) can be performed by the series of processings.

Moreover, with the ultrasonic diagnosing device 1, the region including the cartilage 52 and excluding the subchondral bone 53 is designed as the analysis region, and the three-dimensional Fourier transform is performed targeting the echo signals in the analysis region. Thus, the unnecessary region in calculating the characteristic amount (the region including the subchondral bone 53) can be removed. As a result, the calculation load of the signal processor 10 can be reduced.

Moreover, with the ultrasonic diagnosing device 1, for the knee joint including the proximal end of the thigh bone 51 and a distal end of the shin bone 55, the degeneration degree of the cartilage 52 of the thigh bone 51 can be diagnosed.

Moreover, with the ultrasonic diagnosing device 1, the wave transmitting and receiving surface 4a of the probe 4 is arranged so that the normal direction thereof is oriented toward the cartilage 52 and parallel to the extending direction of the thigh bone 51. Thus, the ultrasonic waves can suitably be transmitted in the depth direction of the cartilage 52.

Moreover, with the ultrasonic diagnosing device 1, the characteristic amount (half width) calculated by the signal processor 10 is displayed on the display unit 5. Thus, the user can visually confirm the characteristic amount as the index indicating the degeneration degree of the cartilage 52.

Although the embodiment of this disclosure is described above, this disclosure is not limited to the above, and without deviating from the scope of this disclosure, various modifications may be applied.

Figure 16:
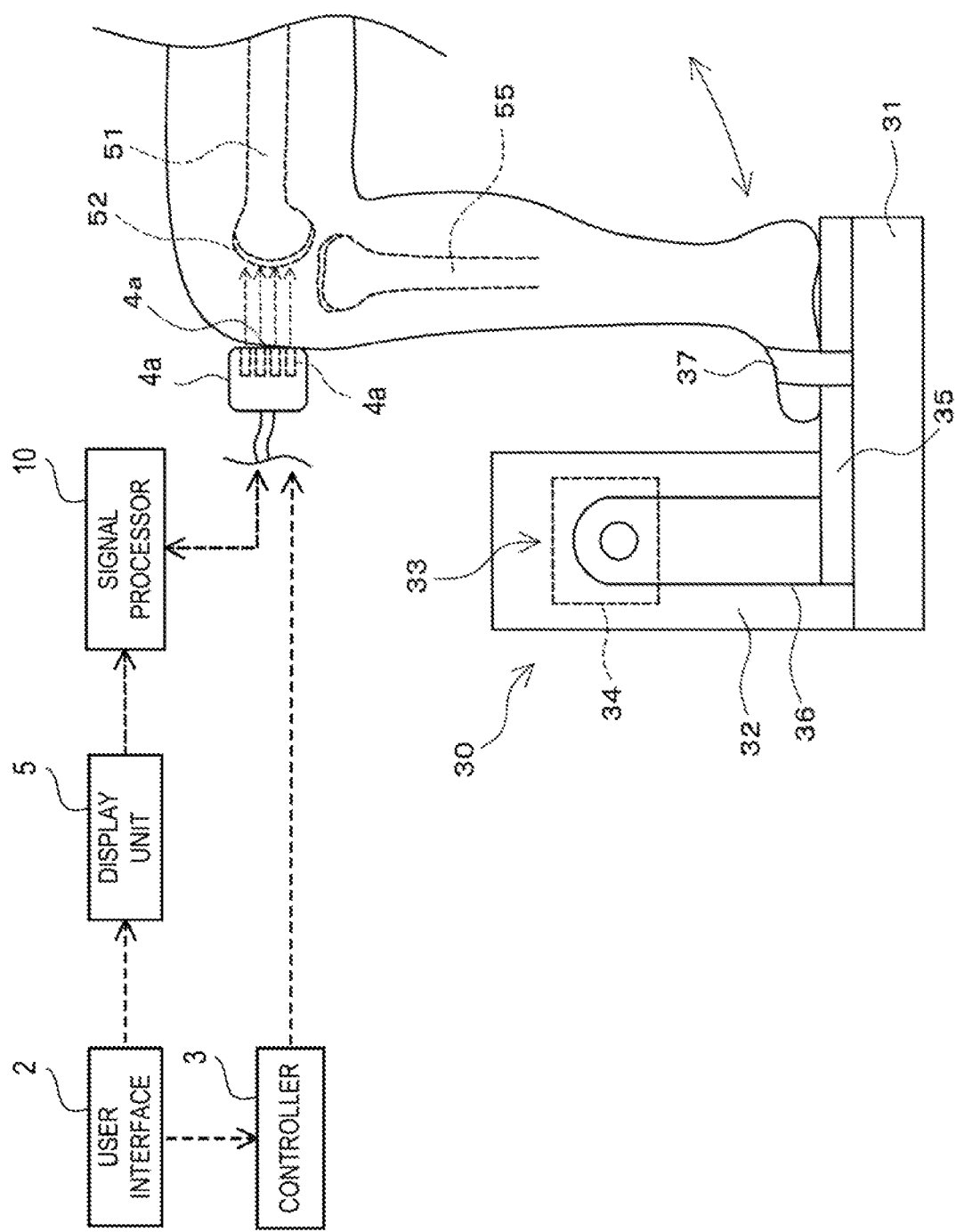
FIG. 16 is a block diagram illustrating a configuration of an ultrasonic diagnosing device according to a modification.

Modifications (1) FIG. 16 is a block diagram illustrating a configuration of an ultrasonic diagnosing device 1a according to a modification. In the above embodiment, the bent state of the knee of the patient is changed by the doctor, for example. However, the ultrasonic diagnosing device 1a of this modification is different from the embodiment described above, and includes an automatic knee bending mechanism 30 capable of automatically changing a bent state of a knee of a patient. Note that, the configuration of the automatic knee bending mechanism 30 described below is an example, and any configuration may be applied as long as it is a mechanism capable of automatically bending a knee of a patient. Moreover, hereinafter, parts that are different from the above embodiment, specifically the configuration and operation of the automatic knee bending mechanism 30, are described, and description of other parts is omitted.

The automatic knee bending mechanism 30 is configured to be capable of swinging a lower part of the knee (under-knee part) of the patient in a state where the patient is seated on a chair and a position of a thigh bone is fixed. Here, the probe 4 is fixed at a position in relation to the thigh bone by a fixing tool (not illustrated) etc. Thus, the knee of the patient is bent into a plurality of states by the automatic knee bending mechanism 30.

The automatic knee bending mechanism 30 includes a pedestal 31, a column 32, and a swinging mechanism 33.

The pedestal 31 is a plate-like part placed on a floor and made of a comparatively heavy metal material, for example. The column 32 is provided to extend upward from the pedestal 31 disposed on the floor. The column 32 is fixed to the pedestal 31.

The swinging mechanism 33 is configured to swing the under-knee part of the patient in front and rear directions of the bending mechanism. The swinging mechanism 33 has an electric motor 34, a foot placing part 35, and a coupling part 36. The electric motor 34 is attached to an upper part of the column 32. The foot placing part 35 is formed into a plate-like shape so that the foot of the patient can be placed thereon, and supported to an upper surface of the pedestal 31. The foot of the patient is fixed to the foot placing part 35 by a fixing belt 37. The coupling part 36 is provided to extend along the column in upper and lower directions of the bending mechanism and a lower end part thereof is fixed to the foot placing part 35 so that a rotational force of the electric motor 34 is transmitted to the foot placing part 35.

In the swinging mechanism 33, when the electric motor 34 rotates, the rotational force is transmitted to the coupling part 36 by a gear (not illustrated) etc. Thus, the foot placing part 35 swings to both sides in arrow directions of FIG. 16, and as a result, the knee of the patient can automatically be bent.

Moreover, with the ultrasonic diagnosing device 1a of this modification, the electric motor 34 rotates normally or inversely so that the knee of the patient is bent and stretched at the given cycle described above, between the first and second bent states illustrated in FIGS. 2(A) and 2(B). During this time, similar to the case of the above embodiment, each oscillator 4b transmits an ultrasonic wave at a given time interval. Thus, with the ultrasonic diagnosing device 1a, echo signals of the cartilage in each of a plurality of bent states can automatically be acquired. Note that, the echo signals acquired as above are processed similarly to the case of the above embodiment.

Figure 17:
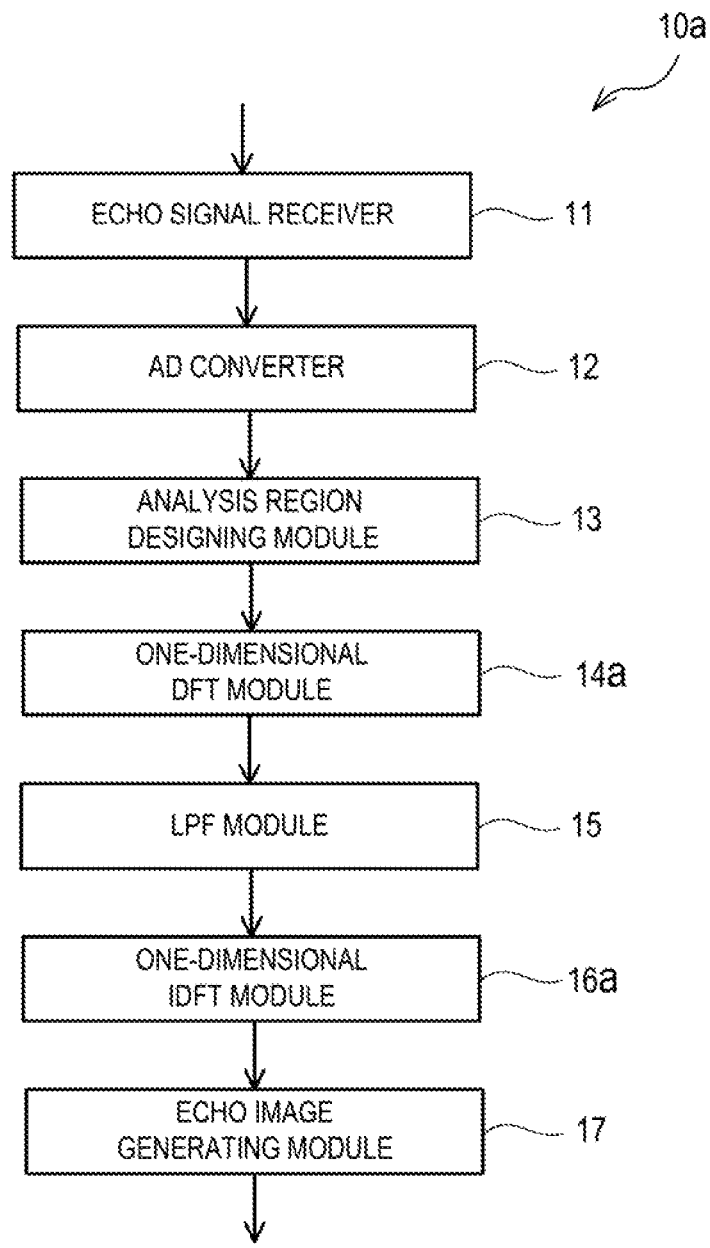
FIG. 17 is a block diagram illustrating a configuration of a signal processor of an ultrasonic diagnosing device according to another modification.

(2) FIG. 17 is a block diagram illustrating a configuration of a signal processor 10a of an ultrasonic diagnosing device according to another modification. In the above embodiment, for the three-dimensional echo data defined in the frame direction, the depth direction of the cartilage, and the direction perpendicular to both the frame and depth directions, the Fourier transform (three-dimensional Fourier transform) is performed in all the directions; however, without limiting to this, the Fourier transform may be performed in the frame direction alone. Thus, compared with the case of the above embodiment, the calculation load on the signal processor 10a when performing the Fourier transform can be reduced. In this modification, the echo image is generated as the information of the cartilage, for example.

Figure 18:
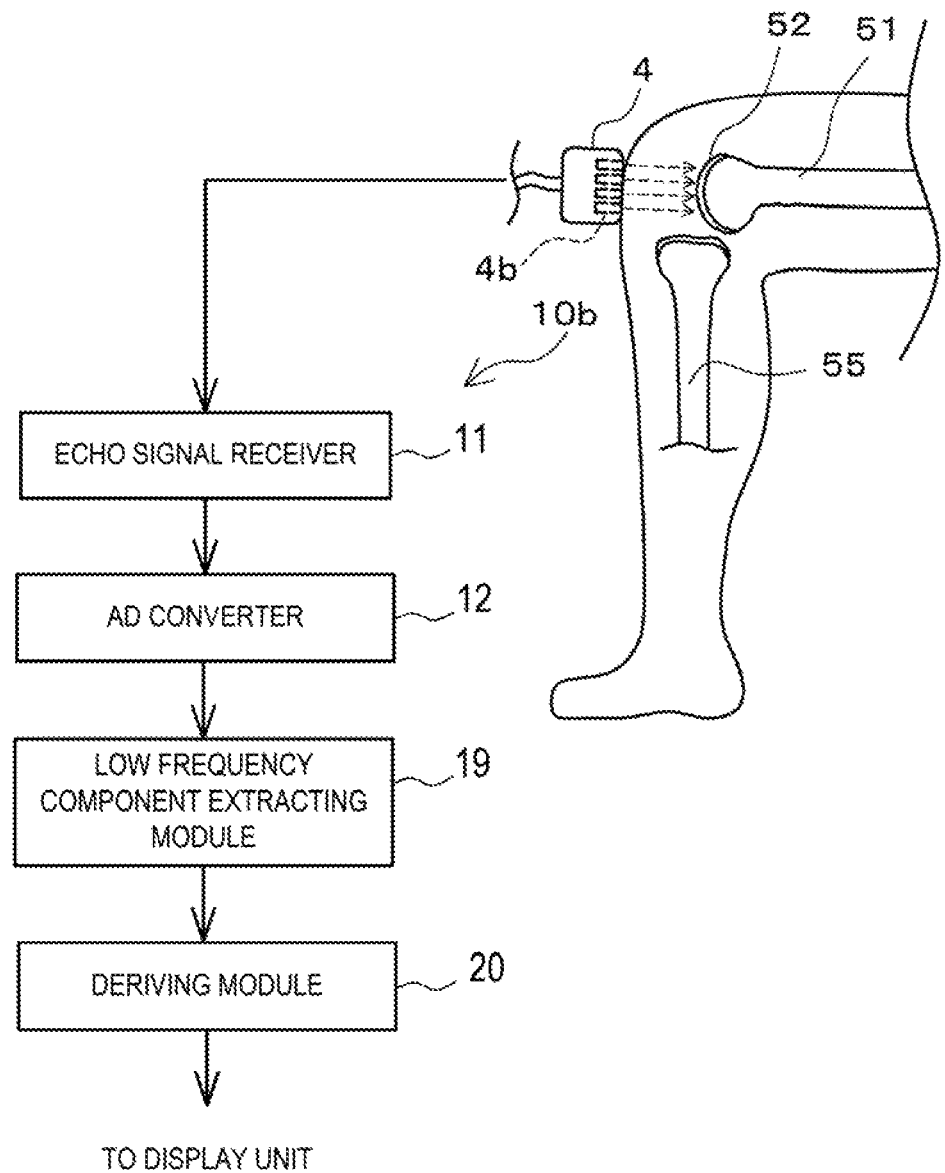
FIG. 18 is a block diagram illustrating a configuration of a signal processor of an ultrasonic diagnosing device according to another modification.

(3) FIG. 18 is a block diagram illustrating a configuration of a signal processor 10b of an ultrasonic diagnosing device according to another modification. The signal processor 10b of this modification includes an echo signal receiver 11, an AD converter 12, a low-frequency component extracting module 19, and a deriving module 20.

The low-frequency component extracting module 19 extracts, from three-dimensional echo data, low-frequency echo data which is echo data of low-frequency components below a given frequency. For example, the low-frequency component extracting module 19 extracts the low-frequency echo data by using a method of LPF (Low Pass Filtering), wavelet transform, convolution, etc. Note that, the wavelet transform is one of methods of frequency analysis, using a wavelet function as a basis function. Further, in the convolution, a function obtained by inverse Fourier transforming a transfer function which is used in the low pass filtering of the above embodiment is convolved with the three-dimensional echo data.

The deriving module 20 derives the information of the cartilage based on the low-frequency echo data extracted by the low-frequency component extracting module 19. The information of the cartilage includes, not only the echo image and the half width which are illustratively described in the above embodiment, but also other information.

(4) In the above embodiment, the example in which the ultrasonic diagnosing device is applied for the cartilage of the thigh bone is described; however, without limiting to this, the ultrasonic diagnosing device of this disclosure may be applied to cartilages of other parts.

(5) In the above embodiment, as the information of the cartilage, the echo image and the half width are displayed on the display unit 5; however, without limiting to this, the power spectrum selected by the power spectrum selecting submodule 18a may be displayed on the display unit 5.

DESCRIPTION OF REFERENCE NUMERALS 1, 1a Ultrasonic Diagnosing Device
4 Probe
4a Wave Transmitting and Receiving Surface
4b Oscillator (Ultrasonic Transmitter, Ultrasonic Receiver)
17 Echo Image Generating Module (Deriving Module)
18 Characteristic Amount Calculating Module (Deriving Module)
19 Low-frequency Component Extracting Module
20 Deriving Module
50 Knee Joint (Joint)

51 Thigh Bone (First Bone)
52 Cartilage (of First Bone)
55 Shine Bone (Second Bone)
60 Soft Tissue

What is claimed is:

1. An ultrasonic diagnosing device, comprising:
an ultrasonic transmitter configured to transmit ultrasonic waves to a cartilage on an end part of a first bone through a soft tissue covering a joint including the end part of the first bone and an end part of a second bone, the ultrasonic transmitter transmitting the ultrasonic waves to the cartilage in a plurality of bent states with different bent angles of the second bone with respect to the first bone, in a state where a relative position of a wave transmitting and receiving surface to the cartilage is fixed, the ultrasonic waves being transmitted and received at the wave transmitting and receiving surface;
an ultrasonic receiver configured to receive echo signals caused by the ultrasonic waves transmitted by the ultrasonic transmitter to obtain echo data, a degeneration degree of the cartilage being diagnosed based on the echo signals received by the ultrasonic receiver, the ultrasonic receiver receiving the echo signals corresponding to a plurality of frames defined in a depth direction of the cartilage and a direction perpendicular to the depth direction, in each of the plurality of bent states; and
processing circuitry configured to
Fourier transform, at least in the frame direction, three-dimensional echo data configured by arraying the echo data of every frame in the frame direction, the depth direction of the cartilage, and a direction perpendicular to both the frame and depth directions,
extract, in a frame direction that is an array direction of the plurality of frames in a time domain, low-frequency echo data from the Fourier transformed three-dimensional echo data, the low-frequency echo data being echo data of a frequency component below a given frequency, and
derive information of the cartilage based on the low-frequency echo data extracted by the processing circuitry,
wherein a bending operation is performed on the second bone at a given cycle between first and second bent states where the bent angle is at a largest angle and a smallest angle among the plurality of bent states, respectively, wherein the ultrasonic transmitter transmits the ultrasonic waves at a given time interval, and
wherein the given frequency is set to be below a frequency expressed as an inverse number of the given cycle.

2. The ultrasonic diagnosing device of claim 1, wherein the processing circuitry is configured to generate an echo image as the information of the cartilage, based on the low-frequency echo data.

3. The ultrasonic diagnosing device of claim 1, wherein the processing circuitry dimensionally Fourier transforms the three-dimensional echo data, and
wherein the
processing circuitry is configured to select low-frequency two-dimensional echo data from the three-dimensional echo data Fourier transformed by the processing circuitry, the low-frequency two-dimensional echo data being two-dimensional echo data at low frequency in the frame direction;
the processing circuitry is configured to calculate total values of echo intensities in regions as a spectral angular characteristic, the regions corresponding to a plurality of angular positions, respectively, set with respect to a reference line passing through an origin of the low-frequency two-dimensional echo data selected by the processing circuitry; and
the processing circuitry is configured to calculate a width of an angle at which the total value becomes a given ratio with respect to a peak value of the spectral angular characteristic calculated by the processing circuitry.

4. The ultrasonic diagnosing device of claim 3, wherein the processing circuitry is further configured to design, in one of the echo data of every frame, an analysis region that is a region defined in the depth direction of the cartilage and the direction perpendicular to the depth direction, including the cartilage, and excluding a subchondral bone to which the cartilage is attached, and
wherein the processing circuitry selects the low-frequency two-dimensional echo data in the analysis region designed by the processing circuitry.

5. The ultrasonic diagnosing device of claim 1, wherein the ultrasonic diagnosing device is used on a thigh bone as the first bone, and a shin bone as the second bone.

6. The ultrasonic diagnosing device of claim 5, wherein the wave transmitting and receiving surface is disposed so that a normal direction thereof is oriented toward the cartilage and parallel to an extending direction of the thigh bone.

7. The ultrasonic diagnosing device of claim 1, further comprising a display unit configured to display the information of the cartilage derived by the processing circuitry.

8. A method of ultrasonic diagnosis, comprising:
transmitting ultrasonic waves to a cartilage on an end part of a first bone through a soft tissue covering a joint including the end part of the first bone and an end part of a second bone, the transmitting the ultrasonic waves to the cartilage in a plurality of bent states with different bent angles of the second bone with respect to the first bone, in a state where a relative position of a wave transmitting and receiving surface to the cartilage is fixed, the ultrasonic waves being transmitted and received at the wave transmitting and receiving surface;
receiving echo signals caused by the ultrasonic waves transmitted by the transmitting the ultrasonic waves to obtain echo data, a degeneration degree of the cartilage being diagnosed based on the echo signals received by the receiving the echo signals, the receiving the echo signals receiving the echo signals corresponding to a plurality of frames defined in a depth direction of the cartilage and a direction perpendicular to the depth direction, in each of the plurality of bent states;
Fourier transforming, at least in a frame direction, three-dimensional echo data configured by arraying the echo data of every frame in the frame direction, the depth direction of the cartilage, and a direction perpendicular to both the frame and depth directions;
extracting, in the frame direction that is an array direction of the plurality of frames in a time domain, low-frequency echo data from the Fourier transformed three-dimensional echo data, the low-frequency echo data being echo data of a frequency component below a given frequency; and
deriving information of the cartilage based on the low-frequency echo data, wherein
wherein a bending operation is performed on the second bone at a given cycle between first and second bent states where the bent angle is at a largest angle and a smallest angle among the plurality of bent states, respectively, wherein the ultrasonic waves are transmitted at a given time interval, and wherein the given frequency is set to be below a frequency expressed as an inverse number of the given cycle.

9. The method of claim 8, wherein an echo image is generated as the information of the cartilage, based on the low-frequency echo data.

10. The method of claim 8, wherein low-frequency two-dimensional echo data is selected from the Fourier transformed three-dimensional echo data, the low-frequency two-dimensional echo data being two-dimensional echo data at low frequency in the frame direction;

wherein total values of echo intensities in regions are calculated as a spectral angular characteristic, the regions corresponding to a plurality of angular positions, respectively, set with respect to a reference line passing through an origin of the selected low-frequency two-dimensional echo data; and wherein a width of an angle is calculated at which the total value becomes a given ratio with respect to a peak value of the spectral angular characteristic.

11. The method of claim 10, wherein, in one of the echo data of every frame, an analysis region is designed that is a region defined in the depth direction of the cartilage and the direction perpendicular to the depth direction, including the cartilage, and excluding a subchondral bone to which the cartilage is attached, and wherein the low-frequency two-dimensional echo data in the analysis region is selected.

12. The method of claim 8, wherein the first bone is a thigh bone, and the second bone is a shin bone.

13. The method of claim 12, wherein the wave transmitting and receiving surface is disposed so that a normal direction thereof is oriented toward the cartilage and parallel to an extending direction of the thigh bone.

14. The method of claim 8, wherein the information of the cartilage derived based on the low-frequency echo data is displayed on a display unit.

* * * * *